(12) United States Patent
Zhang

(10) Patent No.: US 9,220,782 B2
(45) Date of Patent: *Dec. 29, 2015

(54) LONG ACTING SUSTAINED-RELEASE FORMULATION CONTAINING DOPAMINE RECEPTOR AGONIST AND THE PREPARATION METHOD THEREOF

(71) Applicant: Shandong Luye Pharmaceutical Co., Ltd., Shandong (CN)

(72) Inventor: Luping Zhang, Hunan (CN)

(73) Assignee: Shandong Luye Pharmaceutical Co., Ltd., Shandong (CN)

( * ) Notice: Subject to any disclaimer, the term of this patent is extended or adjusted under 35 U.S.C. 154(b) by 22 days.

This patent is subject to a terminal disclaimer.

(21) Appl. No.: 14/182,652

(22) Filed: Mar. 17, 2014

(65) Prior Publication Data

US 2014/0255488 A1    Sep. 11, 2014

Related U.S. Application Data

(63) Continuation of application No. 11/663,411, filed as application No. PCT/CN2005/001521 on Sep. 21, 2005, now Pat. No. 8,691,277.

(30) Foreign Application Priority Data

Sep. 21, 2004 (CN) .......................... 2004 1 0077961

(51) Int. Cl.
| | |
|---|---|
| *A61K 47/34* | (2006.01) |
| *A61K 9/00* | (2006.01) |
| *A61K 31/381* | (2006.01) |
| *A61K 9/16* | (2006.01) |

(52) U.S. Cl.
CPC .............. *A61K 47/34* (2013.01); *A61K 9/0019* (2013.01); *A61K 9/0024* (2013.01); *A61K 9/1647* (2013.01); *A61K 31/381* (2013.01)

(58) Field of Classification Search
CPC . A61K 47/34; A61K 9/0019; A61K 9/20024; A61K 31/381
See application file for complete search history.

(56) References Cited

U.S. PATENT DOCUMENTS

| | | | |
|---|---|---|---|
| 4,166,800 | A | 9/1979 | Fong |
| 6,310,089 | B1 | 10/2001 | Watts et al. |
| 6,455,526 | B1 | 9/2002 | Kohn et al. |
| 6,759,431 | B2 | 7/2004 | Hunter et al. |
| 7,087,247 | B2 | 8/2006 | Li et al. |
| 2003/0166709 | A1 | 9/2003 | Rimpler et al. |
| 2007/0093546 | A1 | 4/2007 | Scheller et al. |

FOREIGN PATENT DOCUMENTS

| | | |
|---|---|---|
| EP | 0 586 838 | 3/1994 |
| EP | 0 930 874 | 7/1999 |
| EP | 1 277 787 | 1/2003 |
| JP | 2003-504972 A | 2/2003 |
| JP | 2004-520269 A | 7/2004 |
| WO | 02/15903 A2 | 2/2002 |
| WO | 02/38646 A2 | 5/2002 |
| WO | 2004/089375 A1 | 10/2004 |

OTHER PUBLICATIONS

Dhirendra et al., "Solid Dispersions: A Review," *Pak. J. Pharm. Sci.* 22(2):234-246, 2009.
International Preliminary Report on Patentability, mailed Mar. 27, 2007, for International Application No. PCT/CN2005/001521.
International Search Report, mailed Nov. 3, 2005, for International Application No. PCT/CN2005/001521.
McRae et al., "Catecholamine-Containing Biodegradable Microsphere Implants as a Novel Approach in the Treatment of CNS Neurodegenerative Disease," *Molecular Neurobiology* 9(1-3):191-205, 1994.
Notice of Reasons for Rejection, dated Apr. 19, 2011, for Japanese Application No. 2007-53749, 2 pages.
Notice of Reasons for Rejection, dated Apr. 19, 2011, for Japanese Application No. 2007-53749, 2 pages. (English Translation).
Written Opinion, mailed Nov. 4, 2005, for International Application No. PCT/CN2005/001521.

*Primary Examiner* — Abigail Fisher
*Assistant Examiner* — Jessica Kassa
(74) *Attorney, Agent, or Firm* — Seed IP Law Group PLLC

(57) ABSTRACT

The present invention relates to a long-acting sustained-release dosage form for treatment of Parkinson Disease, comprising a dopamine receptor agonist and a pharmaceutically acceptable biodegradable polymer accessories, wherein the content of the dopamine receptor agonist in the sustained-release dosage form is 5-50% by weight, and the content of the pharmaceutically acceptable polymer accessories is 50-95% by weight.

10 Claims, 12 Drawing Sheets

LONG ACTING SUSTAINED-RELEASE FORMULATION CONTAINING DOPAMINE RECEPTOR AGONIST AND THE PREPARATION METHOD THEREOF

TECHNICAL FIELD

The present invention relates to long-acting sustained-release dosage forms of dopamine receptor agonists, in particular to injectable sustained-release microspheres, implants and injectable gels of dopaminic drugs and methods for preparing them, and to methods of using these compounds for the manufacture of long-acting sustained release pharmaceuticals, especially microspheres, for the treatment or adjunctive therapy of dopamine receptor associated diseases, and for the treatment of Parkinsonic diseases such as Parkinson's disease or Parkinson's syndrome (hereinafter called as Parkinson Disease).

BACKGROUND ART

Dopamine receptor agonists are important agents for the treatment of Parkinson Disease. At present, clinically used dopamine receptor agonists include dopaminic agonists such as rotigotine, pramipexole, ropinirole, pergolide, terguride, quinagolide, cabergoline and their derivatives and pharmaceutically acceptable salts, and those under clinical trails include sumanirole, SLV-308, adrogolide, ABT-431, Dinapsoline, BAM-1110 and their derivatives and pharmaceutically acceptable salts.

The above medicines usually are administrated orally or transdermally in clinic. Although the oral administration is convenient, patients under advanced Parkinson Disease usually have failure of memory and may forget to take medicines, which will deteriorate their conditions. In addition, the relatively great fluctuation of drug concentration after oral administration may aggravate side-effects and result in "on-off phenomenon", and gastrointestinal tract and liver first pass effect reduce the bioavailability. For example, the bioavailability of rotigotine for oral administration is only 1-5% due to the first pass effect in liver, so that oral dosage forms are not suitable. On the other hand, the transdermal absorption of normal transdermal dosage forms such as ointments, plasters, etc. is not sufficient and often varies because the transdermal absorption is affected by many factors. In addition, transdermal dosage forms are affected by low permeability of skin and thus have low intake, low bioavailability and great individual difference, so that their therapeutic effects are limited, especially for advanced Parkinson Disease patients.

Parenteral administration such as injection can avoid first pass effect, but rotigotine and pramipexole, etc. have a short half-life of only a couple of hours and thus should be administrated several times per day, and other drugs with a relatively longer half-life still should be administrated daily or bidaily and hardly facilitate the administration for patients with Parkinson Disease.

Thus, it is expected to provide a long-acting sustained-release dosage form of dopamine receptor agonist, which is preferably not orally administrated, but intramuscularly injected or subcutaneously administrated, and which can maintain a stable release rate for several weeks, several months or longer so as to reduce as much as possible the pain of patients with Parkinson Disease.

CN1531428A (WO2002/015903) disclosed a Depot-form type sustained-release preparation of rotigotine, wherein the use of a so-called "depot" obtained by suspending rotigotine hydrochloride in an oilly solvent extended the administration interval to more than one day. Although CN1531428A cites the prior art EP0625069 (CN1090172A) which mentioned the preparation of microparticles or micro-capsules (i.e., the microspheres of the present invention) of rotigotine for the implementation of sustained-release, it discloses nothing about the components of micro-capsules or sustained-release microspheres of rotigotine and proportions thereof.

To achieve a long-acting sustained-release preparation that have a administration interval of once weekly or bi-weekly, even once monthly or longer, not only the sustained-release dosage form should stably release drug in vivo for a long period in order to maintain an effective blood drug level in vivo during the period, but also the dosage form should not cause significant side-effects after it is injected into the body, Thus, the use and amounts of both the active component and accessories should be strictly defined in order to implement the administration interval of one or more weeks, even one month and to achieve better therapeutic effects.

CN1531428A and CN1090172A disclose nothing about the sustained-release dosage forms of dopamine receptor agonists and accessories thereof, so that long-acting sustained-release dosage forms (having an administration interval of one or two weeks, even one month or more) of dopamine receptor agonists including rotigotine are actually still unknown.

The inventors of the present invention conducted deep researches for implementation of the long-acting sustained-release of dopamine receptor agonists, and discovered that injectable sustained-release microspheres, implants and injectable gels obtained by using a biodegradable polymer to embed an active component could continuously, stably release the active component for several weeks even several months after they are administrated intramuscularly or subcutaneously, and in the meantime they had high bioavailability, small fluctuation of blood drug level and greatly reduced administration frequency. As compared with traditional oral dosage forms, the side-effects were reduced, the frequency of occurrence of "on-off phenomena" decreased, in the meantime the bioavailability increased significantly, the compliance of patients were improved, and the therapeutic effects of these medicines were achieved to the fullest extent. On this basis, the present invention is carried out.

DISCLOSURES OF THE INVENTION

The object of the present invention is to provide a long-acting sustained-release dosage form of dopamine receptor agonist, such as injectable microspheres, injectable gels and implants, etc. According to the present invention, the administration interval is extended from one day or less to one week, two weeks, one month, two months or more, so that the administration frequency decreases significantly, the first pass effect is avoided, the bioavailability and therapeutic effects are enhanced, and thereby the pain of patients with Parkinson Disease is alleviated remarkably and their life quality is improved.

The above object of the present invention is carried out by the following technical solutions.

The present invention is to provide a long-acting sustained-release dosage form, such as injectable microspheres, injectable gels, implants, etc., especially injectable microspheres, of dopamine receptor agonist, especially rotigotine.

The present invention further provides a method for treatment of Parkinson Disease by using a long-acting sustained-release dosage form.

Concretely, the present invention relates to a long-acting sustained-release dosage form for treatment of Parkinson Disease comprising an effective amount of dopamine receptor agonist and a pharmaceutically acceptable biodegradable polymer accessories, wherein the weight content of the dopamine receptor agonist in the sustained-release dosage form is 5-50%, and the weight content of the pharmaceutically acceptable polymer accessories in the sustained-release dosage form is 50-95%.

The dopamine receptor agonist is one selected from rotigotine, pramipexole, ropinirole, pergolide, cabergoline, terguride, quinagolide, sumanirole, SLV-308, adrogolide (ABT-431), Dinapsoline and BAM-1110 and their derivatives or pharmaceutically acceptable salts, or a combination of two or more of them.

The pharmaceutically acceptable biodegradable polymer accessories is one selected from poly(lactide-glycolide), polylactic acid, polyglycolic acid, poly(3-hydroxy-butyrate), polylactone, polyanhydride, poly(hydroxy-butyrate)-co-(hydroxy-valerate), polypropylene-glucose, poly(lactic acid)-polyglycol, and poly(hydroxyacetic acid)-polyglycol, or a combination of two or more of them.

The long-acting sustained release dosage form of the above dopamine receptor agonist is preferably injectable microspheres, injectable gels, implants, etc.

The above dopamine receptor agonist in the sustained release dosage form is preferably present in the form of solid solution.

In the above long-acting sustained-release dosage form, the pharmaceutically acceptable biodegrade polymer accessories is selected preferably from poly(lactide-glycolide), polylactic acid, polycaprolactone, and polyanhydride, poly(hydroxy-butyrate)-co-(hydroxy-valerate), or a combination of two or more of them, more preferably from poly(lactide-glycolide), polylactic acid, and polyanhydride, or a combination of two or more of them, particularly more preferably poly(lactide-glycolide), more particularly a poly(lactide-glycolide) having a molecular weight of 5,000-100,000 dalton.

In the above poly(lactide-glycolide), the polymerization ratio of lactide to glycolide is between 95:5 and 5:95, preferably between 75:25 and 25:75.

Among the dopamine receptor agonists, their pharmaceutically acceptable salts are salts formed between pharmaceutically active components and inorganic, acids, organic acids or acidic amino acids, wherein the inorganic acids are hydrochloric acid, sulfuric acid, phosphoric acid or nitric acid; the organic acids are citric acid, fumaric acid, maleic acid, acetic acid, benzoic acid, methane sulfonic acid, naphthol sulfonic acid, or p-toluene sulfonic acid; and the acidic amino acid is glutamic acid or aspartic acid, etc.

More concretely, pramipexole or its derivative or pharmaceutically acceptable salt is the free base of pramipexole or pramipexole dihydrochloride, etc.; ropinirole or its derivative or pharmaceutically acceptable salt is the free base of ropinirole or ropinirole hydrochloride, etc.; pergolide or its derivative or pharmaceutically acceptable salt is the free base of pergolide or pergolide methanesulfonate, etc.; cabergoline or its derivative or pharmaceutically acceptable salt is the free base of cabergoline or cabergoline diphosphonate, etc.; terguride or its derivative or pharmaceutically acceptable salt is the free base of terguride or terguride maleate, etc.; quinagolide or its derivative or pharmaceutically acceptable salt is the free base of quinagolide or quinagolide hydrochloride, etc.; sumanirole or its derivative or pharmaceutically acceptable salt is the free base of sumanirole or sumanirole maleate, etc.; SLV-308 or its derivative or pharmaceutically acceptable salt is the free base of SLV-308 or SLV-308 hydrochloride, etc.; adrogolide (ABT-431) or its derivative or pharmaceutically acceptable salt is the adrogolide, adrogolide hydrochloride or transformant A-86929 thereof, etc.; Dinapsoline or its derivative or pharmaceutically acceptable salt is the Dinapsoline or Dinapsoline hydrobromide, etc.; and BAM-1110 or its derivative or pharmaceutically acceptable salt is the BAM-1110 or BAM-1110 maleate, etc.

Among the above dopamine receptor agonists, the most preferable one is rotigotine as shown in the general formula (Ia) and its derivatives or pharmaceutically acceptable salts:

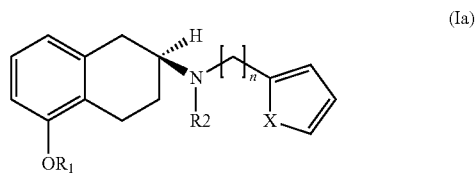

(Ia)

wherein $R_1$ represents hydrogen atom, $C_1$-$C_{10}$ alkylacyl or arylacyl (preferably hydrogen atom, $C_2$-$C_4$ alkylacyl or arylacyl); $R_2$ represents hydrogen atom, $C_1$-$C_{10}$ alkyl, preferably $C_2$-$C_4$ alkyl; X represents carbon atom or nitrogen atom or oxygen atom or sulfur atom; n is an integer selected from 1 to 10 (preferably 1 to 3); the pharmaceutically acceptable salts are formed between the free base of rotigotine and hydrochloric acid, acetic acid, phosphoric acid, sulfuric acid, lactic acid or citric acid. The preferable rotigotine type compounds are rotigotine acetate, rotigotine benzoate, rotigotine propionate, rotigotine butyrate and rotigotine iso-butyrate and hydrochlorides thereof.

In the above long-acting sustained-release dosage form, the weight content of dopamine receptor agonist is preferably from 10% to 40%, and the weight content of the pharmaceutically acceptable polymer accessories is from 60% to 90%; and the weight ratio of the dopamine receptor agonist to the pharmaceutically acceptable polymer accessories is (10-30):(90-70).

When the above long-acting sustained-release dosage form is injectable sustained-release microspheres, its particle diameter is preferably between 50 and 200 micrometers. The other contents and merits of the present invent are further illustrated in the following details.

BEST MODES FOR CARRYING OUT THE PRESENT INVENTION

Figure 1:
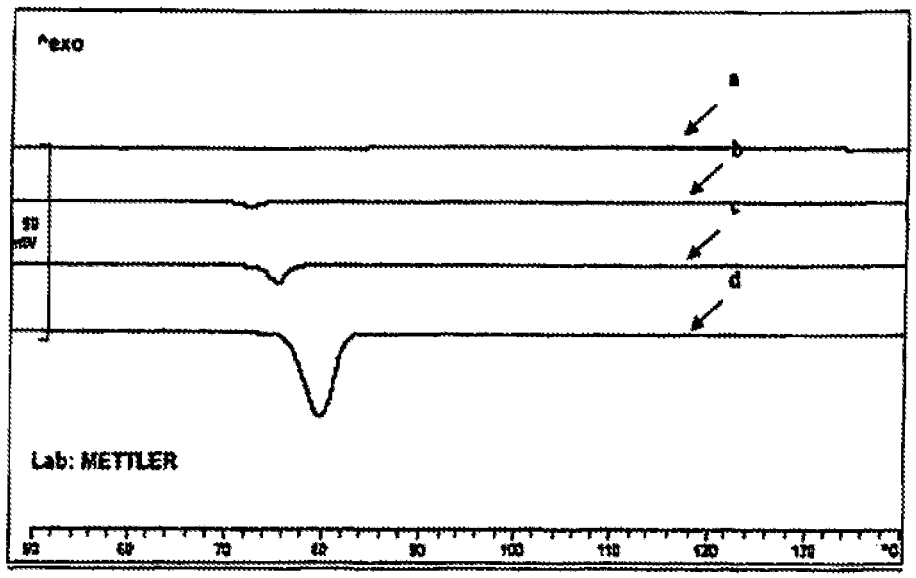
FIG. 1 is the differential thermal analysis diagram of rotigotine microspheres with different contents.

The long-acting sustained-release dosage form of the present invention for treatment of Parkinson Disease comprises an effective amount of dopamine receptor agonist and a proper amount of pharmaceutically acceptable biodegradable polymer accessories, and specific examples include injectable sustained-release microspheres, injectable gels, implants, etc.

Obviously, besides the above main components (i.e., the dopamine receptor agonist as active component, and the pharmaceutically acceptable polymer accessories), the sustained-release dosage form of the present invention may further comprise other components essential for preparation and administration of the dosage form, such as solvents, buffers, isotonizing agents, etc., which are not limited in the present invention. All mentioned proportions or contents concerning to sustained-release dosage form are based on the total amount of the active component and the pharmaceutically acceptable polymer accessories.

Wherein, the dopamine receptor agonist is one selected from rotigotine, pramipexole, ropinirole, pergolide, cabergoline, terguride, quinagolide, sumanirole, SLV-308, adrogolide (ABT-431), Dinapsoline and BAM-1110 and their derivatives or pharmaceutically acceptable salts, or a combination of two or more of them.

The above mentioned pharmaceutically acceptable salts are salts formed between dopamine receptor inhibitors and pharmaceutically acceptable acids, specifically inorganic acids, organic acids or acidic amino acids, wherein the inorganic acids are hydrochloric acid, sulfuric acid, phosphoric acid or nitric acid; the organic acids are citric acid, fumaric acid, maleic acid, acetic acid, benzoic acid, methane sulfonic acid, naphthol sulfonic acid, or p-toluene sulfonic acid; and the acidic amino acid is glutamic acid or aspartic acid, etc.

In the present invention, the pramipexole or its derivative or pharmaceutically acceptable salt is the relevant compounds as disclosed in EP186087 and U.S. Pat. No. 4,886,812 and other improved compounds or pharmaceutically acceptable salts as disclosed in other documents, preferably the free base of pramipexole or pramipexole dihydrochloride, etc.

Ropinirole or its derivative or pharmaceutically acceptable salt is the relevant compounds as disclosed in U.S. Pat. No. 4,452,808 or the ropinirole derivatives or pharmaceutically acceptable salts thereof as disclosed by other documents, preferably the free base of ropinirole or ropinirole hydrochloride, etc.

Pergolide or its derivative or pharmaceutically acceptable salt is the selected from the relevant compounds as disclosed in U.S. Pat. No. 4,166,182 or the pergolide derivatives or pharmaceutically acceptable salts thereof as disclosed by other documents, preferably the free base of pergolide or pergolide methanesulfonate, etc.

Cabergoline or its derivative or pharmaceutically acceptable salt is the selected from the relevant compounds as disclosed in U.S. Pat. No. 4,526,892 and EP888243 or the cabergoline derivatives or pharmaceutically acceptable salts thereof as disclosed by other documents, preferably the free base of cabergoline or cabergoline diphosphonate, etc.

Terguride or its derivative or pharmaceutically acceptable salt is the selected from the relevant compounds as disclosed in U.S. Pat. No. 3,953,454 and DE3001752 or the terguride derivatives or pharmaceutically acceptable salts thereof as disclosed by other documents, preferably the free base of terguride or terguride maleate, etc.

Quinagolide or its derivative or pharmaceutically acceptable salt is the selected from the relevant compounds as disclosed by U.S. Pat. No. 4,565,818 and EP77754 or quinagolide derivatives or pharmaceutically acceptable salts thereof as disclosed by other documents, preferably the free base of quinagolide or quinagolide hydrochloride, etc.

Sumanirole or its derivative or pharmaceutically acceptable salt is the selected from the relevant compounds as disclosed in U.S. Pat. No. 5,478,734 or the sumanirole derivatives or pharmaceutically acceptable salts thereof as disclosed by other documents, preferably the free base of sumanirole or sumanirole maleate, etc.

SLV-308 or its derivative or pharmaceutically acceptable salt is the selected from the relevant compounds as disclosed in WO00/29397 or SLV-308 derivatives or pharmaceutically acceptable salts as disclosed by other documents, preferably the free base of SLV-308 or SLV-308 hydrochloride, etc.

Adrogolide (ABT-431) or its derivative or pharmaceutically acceptable salt is the selected from the relevant compounds as disclosed in WO9422858 or the adrogolide derivatives or pharmaceutically acceptable salts thereof as disclosed by other documents, preferably the free base of adrogolide, adrogolide hydrochloride or transformant A-86929 of adrogolide, etc.

Dinapsoline or its derivative or pharmaceutically acceptable salt is the selected from the relevant compounds as disclosed in WO97/06799 or Dinapsoline derivatives or pharmaceutically acceptable salts thereof as disclosed by other documents, preferably the free base of Dinapsoline or Dinapsoline hydrobromide, etc.

BAM-1110 or its derivative or pharmaceutically acceptable salt is the relevant compounds as disclosed in U.S. Pat. No. 4,713,457 or BAM-1110 derivatives or pharmaceutically acceptable salts thereof as disclosed by other documents, preferably the free base of BAM-1110 or BAM-1110 maleate, etc.

In the long-acting sustained-release dosage form of dopamine receptor agonist of the present invention, the active component is most preferably rotigotines, i.e., rotigotine compounds and derivatives or pharmaceutically acceptable salts thereof.

The structural formula of rotigotines is shown in the general formula (Ia):

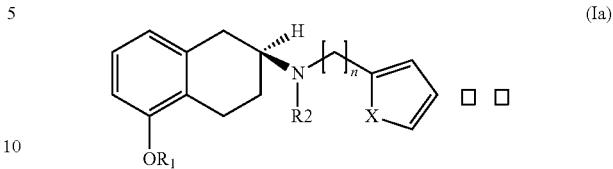

wherein $R_1$ represents hydrogen atom, $C_1$-$C_{10}$ alkylacyl or arylacyl, preferably hydrogen atom, $C_2$-$C_4$ alkylacyl or arylacyl; $R_2$ represents hydrogen atom, $C_1$-$C_{10}$ alkyl (preferably $C_1$-$C_5$ alkyl); X represents carbon atom or nitrogen atom or oxygen atom or sulfur atom; n is an integer selected from 1 to 10, preferably 1 to 3, most preferably 2; the pharmaceutically acceptable salts thereof are formed between the free base of rotigotine and hydrochloric acid, acetic acid, phosphoric acid, sulfuric acid, lactic acid or citric acid; the preferable rotigotine compounds and derivatives thereof are preferably rotigotine, rotigotine acetate, rotigotine propionate, rotigotine benzoate, as well as rotigotine butyrate and rotigotine iso-butyrate and hydrochlorides thereof, specifically the compounds (I), (II), (III) or (IV) as shown in the following table.

| Ccompound | $R_1$ | $R_2$ | X | n |
|---|---|---|---|---|
| I | Hydrogen | n-propyl | S | 2 |
| II | Acetyl | n-propyl | S | 2 |
| III | Propionyl | n-propyl | S | 2 |
| IV | Benzoyl | n-propyl | S | 2 |
| V | Butyl | n-propyl | S | 2 |
| VI | Iso-butyl | n-propyl | S | 2 |

If the compound (I) is used as mother nucleus of rotigotine for denomination, the compounds (II)-(VI) are named as rotigotine acetate, rotigotine propionate, rotigotine benzoate, rotigotine butyrate and rotigotine iso-butyrate. Among the above compounds, rotigotine is the most preferable one, i.e., the compound (I), and its pharmaceutically acceptable salt is rotigotine hydrochloride.

The active component in the long-acting sustained-release dosage form of the present invention may further be the metabolites or transformants (prodrugs) thereof, besides the above compounds.

The pharmaceutically acceptable polymer accessories of the present invention is selected from poly(lactide-glycolide), polylactic acid, polyglycolic acid, poly(3-hydroxy-butyrate), polylactone, polyanhydride, poly(hydroxy-butyrate)-co-(hydroxy-valerate), polypropylene-glucose, poly(lactic acid)-polyglycol, and poly(hydroxyacetic acid)-polyglycol, or a combination of two or more of them, wherein the molecular weight thereof is between 2,000 and 1,000,000 dalton, and the pharmaceutically acceptable polymer accessories of the present invention is preferably poly(lactide-glycolide), polylactic acid, polycaprolactone, polyanhydride, poly(hydroxy-butyrate)-co-(hydroxy-valerate), or a combination of two or more of them.

When the sustained-release dosage form is injectable microspheres, the pharmaceutically acceptable polymer accessories of the present invention is more preferably a poly(lactide-glycolide) having a molecular weight of 2,000-100,000 dalton, more preferably 5,000-50,000, wherein the polymerization ratio of lactide to glycolide in the poly(lactide-glycolide) is between 95:5 and 5:95, preferably between 75:25 and 25:75, most preferably about 50:50.

When the sustained-release dosage form is injectable gels or implant, the pharmaceutically acceptable polymer of the present invention is preferably polylactic acid) or polyanhydride having a molecular weight of between 2,000 and 1,000,000 dalton.

In the long-acting sustained-release dosage form of the present invention, the weight percentage content of the dopamine receptor agonist in the sustained-release dosage form is 5-50%, preferably 10-50%, more preferably 10-40%, most preferably 10-30%; and the weight content of the pharmaceutically acceptable polymer accessories is 50-95%, preferably 50-90%, more preferably 60-90%, most preferably 70-90%.

If the weight content of the dopamine receptor agonist is less than 5%, the blood drug level cannot be maintained at a sufficiently high level; while if the weight content is higher than 50%, the release of drug may be unstable and side effects may occur.

When the content of dopamine receptor agonist in the sustained-release dosage form is at a certain level, this drug is homogeneously distributed in the pharmaceutically acceptable accessories and is present in a state of solid solution, which ensures the stable release of drug. On the contrary, if the content is relatively high, the drug is not present in a state of solid solution in the dosage form, and the drug release may be unstable. This is more important for the sustained-release microspheres, and it is deemed as an important mechanism of causing sudden-release of drug that the drug is not present in a state of solid solution in microspheres. As for other sustained-release dosage forms such as injectable gels or implants, since they do not flow with blood as microspheres and have less possibility to generate sudden-release, the content range may be properly broadened, but should not exceed 50%.

This is further illustrated by taking rotigotine microspheres as example. The differential thermal analysis spectra of rotigotine microspheres with different contents as made according to the method of following examples and rotigotine per se as control are shown in FIG. 1. In FIG. 1, the curve a is the differential thermal curve when the rotigotine load is less than 30%, the curve b is the differential thermal curve when the rotigotine load is 34%, the curve c is obtained when the load is 47%, and the curve d is the differential thermal curve of rotigotine per se.

According to FIG. 1, rotigotine is a crystalline solid and has a melting point of 79-80° C. (see the curve d). When the drug load is less than 30% in microspheres, rotigotine has a good compatibility with the copolymer of lactic acid and hydroxyacetic acid, and rotigotine is essentially completely dissolved in the polymer carrier and forms a solid solution so that the melting point of rotigotine is not observed (see the curve a). However, when the drug load reaches to 34%, the melting point of rotigotine is observed at 73° C. (see the curve b) and rises with the increase of the drug load, for example, when the drug load is 47%, the melting point of rotigotine is 76° C. (see the curve c), and the heat absorption area increases as well, which means that when the drug load is more than 34%, not all rotigotine is present in solid solution state, and a part of rotigotine becomes crystal, so that the microspheres are not of a homogeneous phase system and contain separated phases, while this kind of phase separation not only affects the physical and mechanical properties of the microspheres, but also results in a higher initial release and a quicker sustained-release.

When the content of rotigotine is constant, the melting point and heat absorption area of rotigotine in microspheres are lower or smaller than the melting point and heat absorption area of pure rotigotine (see the curve d), because the rotigotine crystal in microspheres is not perfect and only a part of rotigotine is crystallized.

The present invention provides not only a long-acting sustained-release dosage form containing one of the above pharmaceutical compounds as single active component, but also a long-acting sustained-release dosage form containing two or more of the above pharmaceutical compounds in combination as active components as well as pharmaceutically acceptable polymer accessories, which dosage form, such as long-acting sustained-release injectable microspheres, injectable gels or implants, has same or different sustained-release effects and implements the synergistic effects of several different active components.

The long-acting sustained-release dosage forms of the present invention, such as injectable sustained-release microspheres, implants or injectable gels, have an administration interval of at least one week, preferably at least two weeks, wherein the implants and gels have an administration interval of at least one month. The injectable microspheres, implants and injectable gels of the present invention are separated illustrated as follows.

Sustained-release Microspheres

The sustained-release microspheres of dopamine receptor agonist of the present invention (also called as injectable microspheres, microspheres in the present invention) are prepared according to conventional methods in the art.

The sustained-release injectable microspheres of dopamine receptor agonist of the present invention have a diameter preferably between 1 and 250 micrometers, most preferably between 50 and 200 micrometers, so as to maintain a certain time-effect, biodegradability and to avoid the effects on blood circulation, because microspheres with excessively small diameter can hardly maintain pharmaceutical action for a long time and may obstacle blood capillary and influence blood circulation, while microspheres with excessively large diameter have a too slow initial release and cannot reach a therapeutically effective blood drug level.

For the sustained-release microspheres of the present invention, the load of active component should not be excessively low, otherwise the excessively large amount of microspheres injected to patients may cause side-effects such as pain and so on; while if the load is excessively high, serious sudden-release and overdose may occur when the microspheres are administrated to patients.

Specifically, the weight content of the active component is 5-50%, preferably 10-40%, most preferably 10-30%, and the weight content of the pharmaceutically acceptable degradable polymer accessories is 50-95%, preferably 60-90%, most preferably 70-90%.

According to the following examples and experiments, the blood drug level cannot be maintained at a sufficiently high level when the weight content of dopamine receptor agonist is less than 5%; on the contrary, when the weight content is higher then 50%, the drug release is unstable, and suddenrelease and side-effects may occur.

According to the following examples and experiments, the proper drug load should be not higher than 50%, preferably less than 30%. According to the minimum blood drug level for therapy and the acceptable injection amount of microspheres, the drug load is most preferably between 10% and 30%.

In the long-acting sustained-release microspheres of the present invention, the dopamine receptor agonist is selected preferably from rotigotine and derivatives or pharmaceutically acceptable salts thereof, wherein rotigotine and derivatives thereof are preferably rotigotine, rotigotine acetate, rotigotine propionate, rotigotine butyrate, rotigotine isobutyrate, and rotigotine benzoate, and their pharmaceutically acceptable salts are preferably hydrochlorides.

In the injectable microspheres of rotigotine and derivatives or pharmaceutically acceptable salts thereof of the present invention, based on the total weight of rotigotine compound and pharmaceutically acceptable polymer accessories, rotigotine is 5-50%, preferably 10-50%, more preferably 10-40%, most preferably 10-30%, and the pharmaceutically acceptable polymer accessories is 50-95%, preferably 50-90%, more preferably 60-90%, most preferably 70-90%.

When the microspheres of rotigotine and derivatives or pharmaceutically acceptable salts thereof of the present invention are prepared, rotigotine and derivatives or pharmaceutically acceptable salts should be in solid solution state, i.e., the active component is not separated from accessories and is present in homogeneous phase.

The microspheres of the present invention are prepared according to conventional methods for preparation of microspheres in the art, such as spray-drying method, solvent-volatilizing method, and atomizing-extracting method, but are not limited to these methods.

When solvent-volatilizing method is employed to prepare the microspheres of the present invention, dopamine receptor agonist and pharmaceutically acceptable biodegradable accessories are dissolved in an organic solvent to form an organic phase. In addition, a pharmaceutically acceptable water soluble polymer is used to form a continuous water phase. The organic phrase is injected through tubules into the continuous phase and sufficiently emulsified under vigorous agitation of mechanical stirring or ultrasonic wave to form microspheres, then the organic solvent is volatized, and the formed microspheres are separated by filtration and dried. If necessary, the microspheres are further subjected to conventional post treatment such as water-washing and grading, drying treatment such as vacuum drying or freeze-drying, and subpackage.

During the above operations, the dopamine receptor agonist and the pharmaceutically acceptable biodegradable accessories are those aforementioned. In view of operation, the organic solvent should be a sufficiently volatile, low-residual and low-boiling point organic solvent, for example, dichloromethane, chloroform, ethyl acetate, ethyl ether, and mixture solvents of their combination, The pharmaceutically acceptable polymer used for forming the continuous water phase is selected from polyvinyl alcohol, sodium carboxymethylcellulose, polyvinyl pyrrolidone, sodium polymethacrylate, sodium polyacrylate, or a combination of two or more of them, but is not limited to these.

When the organic phase is prepared, the contents of dopamine receptor agonist and the pharmaceutically acceptable degradable accessories in the organic solvent are not limited if they can be dissolved in the organic solvent, but in view of the balance between possible concentration and viscosity and the reduction of organic solvent, the concentration is preferably 1-30% (w/v). When polyvinyl alcohol, sodium carboxymethylcellulose, polyvinyl pyrrolidone, sodium polymethacrylate, sodium polyacrylate, or a combination of two or more of them is used for preparing the continuous water phase, its concentration is not specifically limited, but according to its solubility in water, its concentration in the water phase is preferably 0.01-12% (w/v), more preferably 0.01-10.0% (w/v), more preferably 0.1-5% (w/v). When the organic phase is injected into the water phase under vigorous agitation to form microspheres, the volume ratio of the organic phase to the water phase is at a level so that the organic phase is sufficiently dispersed in the water phase to form microspheres with sufficiently small particle size and homogeneousness. However, if too much water phase is used, the post treatment is complex and the cost increases, so that in view of these aspects, the volume ratio of the organic phase to the water phase is from about 1:4 to 1:100.

The microspheres can also be prepared by spray-drying method. When the sustained-release microspheres of dopamine receptor agonist are prepared by spray-drying method, the dopamine receptor agonist and the pharmaceutically acceptable biodegradable accessories are sufficiently dissolved in an organic solvent to form an organic solution, then the solution is filtered and processed by a conventional spray-drying method to form microspheres. If necessary, the microspheres are subjected to conventional post treatment such as water washing and grading, and then subpackaged.

When the above spray-drying method is employed to prepare microspheres, the organic solvent can be dichloromethane, chloroform, ethyl acetate, dioxane, ethyl ether, acetone, tetrahydrofuran, glacial acetic acid, and a mixture solvent of them, but is not limited to these.

When the organic phase is prepared, the content of the pharmaceutically acceptable degradable accessories in the organic solvent is not limited if these accessories can be dissolved in the organic solvent, but in a view of the balance between the possible concentration and the reduction of organic solvent, the concentration is preferably 1-30% (w/v).

The microspheres can also be prepared by employing an atomizing-extracting method. When the atomizing-extracting method is employed to prepare the microspheres of dopamine receptor agonist, the dopamine receptor agonist and pharmaceutically acceptable biodegradable polymer accessories are sufficiently dissolved in an organic solvent (which can dissolve the dopamine receptor agonist and the pharmaceutically acceptable biodegradable polymer accessories) to form an organic solution, then the organic solution is atomized into an organic non-solvent (an organic solvent that cannot dissolve the dopamine receptor agonist and the pharmaceutically acceptable biodegradable polymer accessories) or water, and microspheres are obtained by extracting. If necessary, the microspheres are further subjected to conventional post treatment such as water-washing and grading, and then subpackaged.

When the microspheres are prepared according to the above atomizing-extracting method, the organic solvent is dichloromethane, chloroform, ethyl acetate, dioxane, ethyl ether, acetone, tetrahydrofuran, benzene, toluene, glacial acetic acid, and a mixture solvent of them, but is not limited to these. The said organic non-solvent is methanol, ethanol, propanol, isopropanol, petroleum ether, alkane, paraffine, and a mixture solvent thereof, but is not limited to these.

When the organic phase is prepared, the content of the pharmaceutically acceptable accessories in the organic solvent is not limited if these accessories can be dissolved in the organic solvent, but in a view of the balance between the possible concentration and the reduction of organic solvent, the concentration is preferably 1-30% (w/v).

As comparing the solvent-volatilizing method and the spray-drying method for the preparation of microspheres, in view of the particle homogeneousness and the simple operation, the spray-drying method is preferred, while in view of the reduction of initial release, the solvent-volatilizing method is preferred.

After the microspheres of dopamine receptor agonist of the present invention are formed, they may be subjected to particle grading or not if particle size is sufficiently homogeneous, washing, drying and subpackage according to prescribed dosage, and then they may be processed to form injectable powder from which an injection can be prepared in situ. The injectable powder may be prepared directly from the said microspheres from which an injection solution can be prepared in situ by mixing and suspending with physiological saline; or the microspheres are mixed with prescribed amounts of isotonic salt, mannitol, glucose, etc., and an injection solution can be prepared in situ by adding an prescribed amount of injectable pure water; or the microspheres of an injection amount are suspended and then freeze-dried in advance, and water is added before using. In the present invention, the method for treatment of diseases associated with dopamine receptor and the method for treatment of Parkinson Disease are carried out by giving patients needing the above treatments the injection solution of dopamine receptor agonist of the present invention. Any administration method of using injection can be used, for example, intramuscular injection, subcutaneous injection, intradermal injection, intraabdominal injection, etc. In view of ease administration, intramuscular injection and subcutaneous injection are preferred.

The administration dosage of the sustained-release microspheres of dopamine receptor agonist of the present invention, taking rotigotine as example, is 10-400 mg of rotigotine per injection for a patient having a body weight of 60 kg, and the injection volume is 1-5 ml, preferably 1-3 ml. The injection administration interval is at least one week or two weeks. Specific conditions are properly adjusted according to patient's age, body weight and conditions.

The administration interval of the sustained-release microspheres of dopamine receptor agonist of the present invention is at least one week, preferably at least two weeks, more preferably at least 20 days, even more than 2 months. Thus, the life quality of patients with Parkinson Disease is improved, and the problem of daily administration is overcome.

The long-acting sustained-release microspheres of the present invention have a high encapsulation rate, a continuous and stable drug release, a stable and effective blood drug level in patient's body, better therapeutic effects and low side-effects, and thus overcome the drawbacks of conventional dosage forms and can bring about good therapeutic effects in treatment of Parkinson Disease.

1. Implants

The active components and pharmaceutically acceptable polymer accessories used in the implants of the present invention are essentially similar with those of the above sustained-release microspheres, so that only their differences are illustrated as follows.

According to the above statements, since the implants are embedded topically, proviso that a proper release is ensured, the content of active component can be at a relatively high level, but appropriately not more than 50%.

The implants of the present invention can be prepared according to conventional methods in the art, preferably by the following method: dissolving the dopamine receptor agonist in an organic solvent, sufficiently and homogeneously mixing with a pharmaceutically acceptable polymer accessories, heating and extruding to form rod-shape implants, wherein the organic solvent is methanol, ethanol, isopropanol, ethyl ether, butyl ether, methyl ethyl ether, methyl butyl ether, hexane, heptane, octane, or a mixture thereof, but is not limited to these.

The implants of the present invention can be embedded subcutaneously by conventional operation or injection in clinic, and drug disperses from the implants into blood slowly and enters into circulation system. The administration interval of the implants of the present invention is at least one month, even 4-6 months, which greatly facilitates the administration for patients with Parkinson Disease.

2. Injectable Gels

The active components and pharmaceutically acceptable polymer accessories used in the injectable gels of the present invention are essentially similar with those of the above sustained-release microspheres, so that only their differences are illustrated as follows.

According to the above statements, since the injectable gels form topical implants after they are injected in body, proviso that the active component can be dissolved into an organic solvent and a proper release is ensured, the content of the active component can be at a relatively high level, but appropriately not more than 50%.

The injectable gels of the present invention can be prepared according to conventional methods in the art, preferably by the following method: weighing dopamine receptor agonist and pharmaceutically acceptable polymer accessories, dissolving them into an organic solvent to obtain an injectable gel. The solvent is a pharmaceutically acceptable organic solvent such as N-methyl pyrrolidone, DMSO, etc., but is not limited to these two solvents. In clinic, the injectable gel of the present invention can be directly injected subcutaneously or intramuscularly, then the organic solvent quickly diffuses into body liquid and is metabolized, the gel is solidified subcutaneously or intramuscularly to form an implant, and the drug gradually diffuses from the implant into circulation system in vivo. The administration interval of the injectable gels of the present invention is at least two weeks. Thus, the injectable gels of the present invention are ease for administration and overcome the drawbacks of conventional oral dosage forms.

EXAMPLES

The long-acting sustained-release dosage forms of dopamine receptor agonist of the present invention are further illustrated by the following examples and experiments, but these examples are not intended to limit the present invention.

In the following examples, the diameters of microspheres were measured by L2000 type automatic laser particle size meter (Beckman Coulter) that was well known in the art. The concentrations were measured by high performance liquid chromatograph (HPLC) according to methods as disclosed in documents, such as Journal of Modern Applicable Pharmacy, 1993, 10(1), pages 51-52, and Journal of Chinese Medical and Pharmaceutical Industry, 1999, 30(8), pages 363-365, etc.

Example 1

Figure 2:
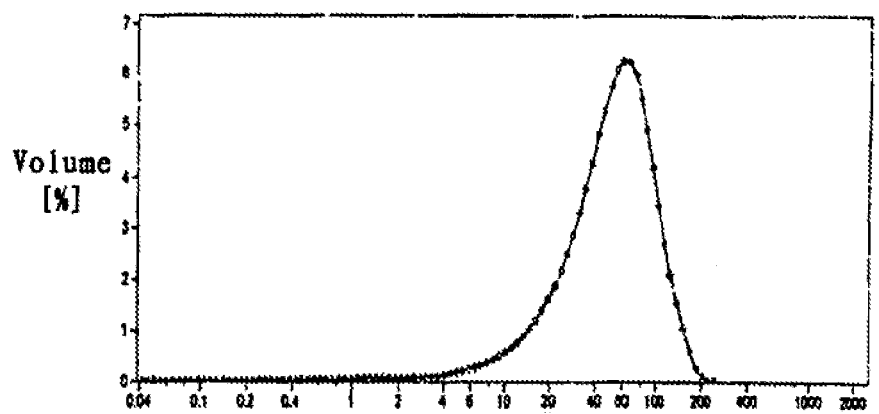
FIG. 2 is the particle diameter distribution diagram of the sustained-release microspheres obtained in Example 1.
Figure 3:
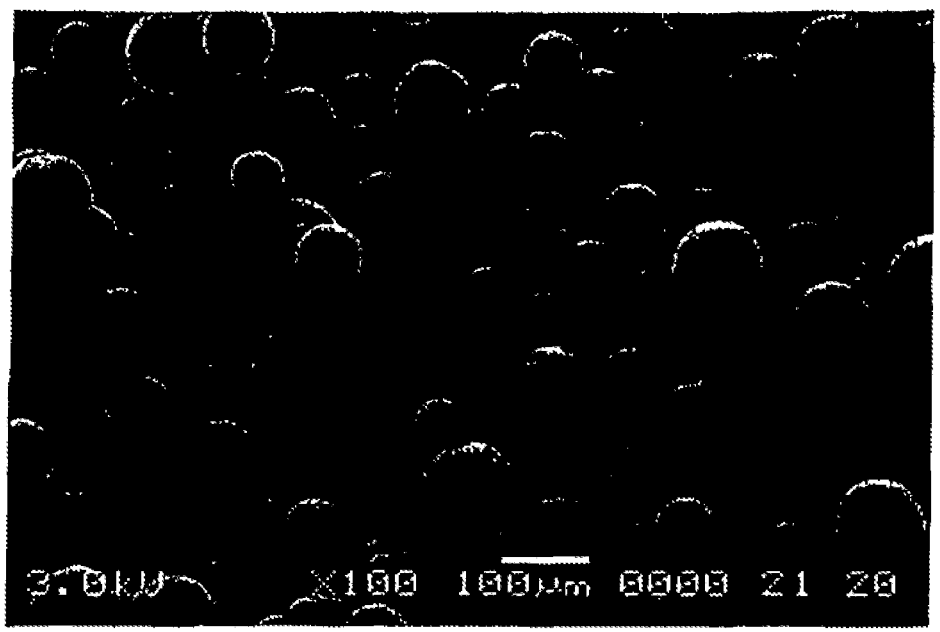
FIG. 3 is the scanning electron microscope photo of the sustained-release microspheres obtained in Example 1.
Figure 4:
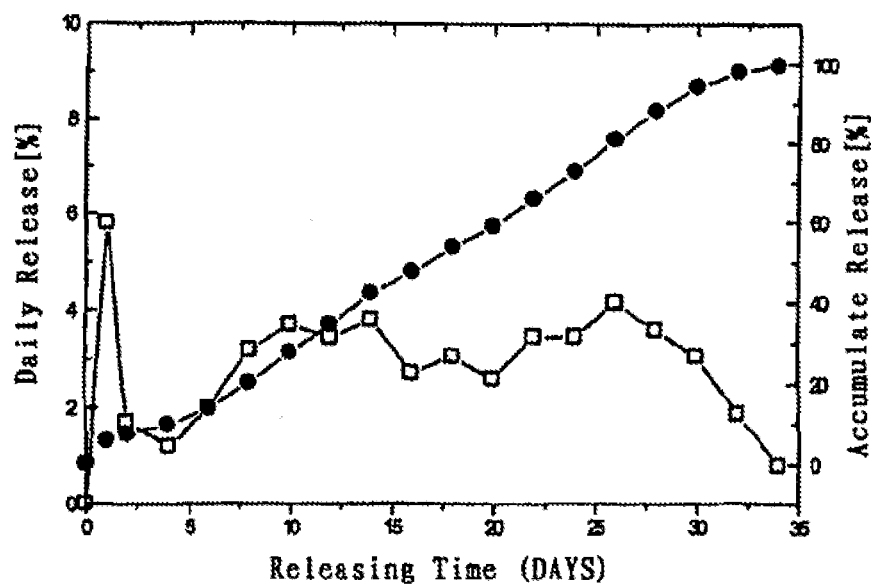
FIG. 4 is the polygonal diagram of daily release rate and accumulative release rate of the sustained-release microspheres obtained in Example 1 in a simulative release liquid having a pH value of 7.4, wherein □ represents daily release, and ● represents accumulative release.
Figure 5:
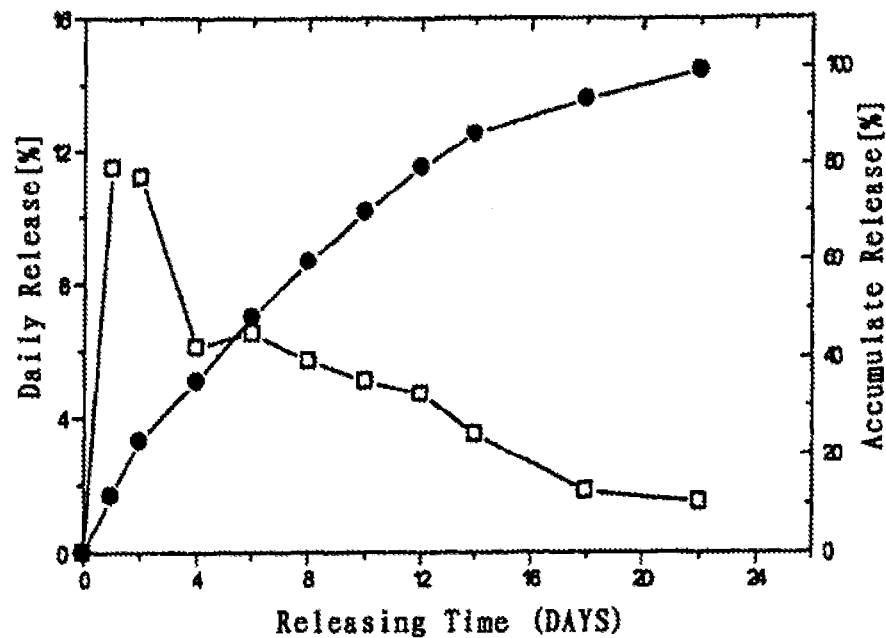
FIG. 5 is the polygonal diagram of daily release rate and accumulative release rate of the sustained-release microspheres obtained in Example 2 in a simulative release liquid having a pH value of 7.4, wherein □ represents daily release, and ● represents accumulative release.
Figure 6:
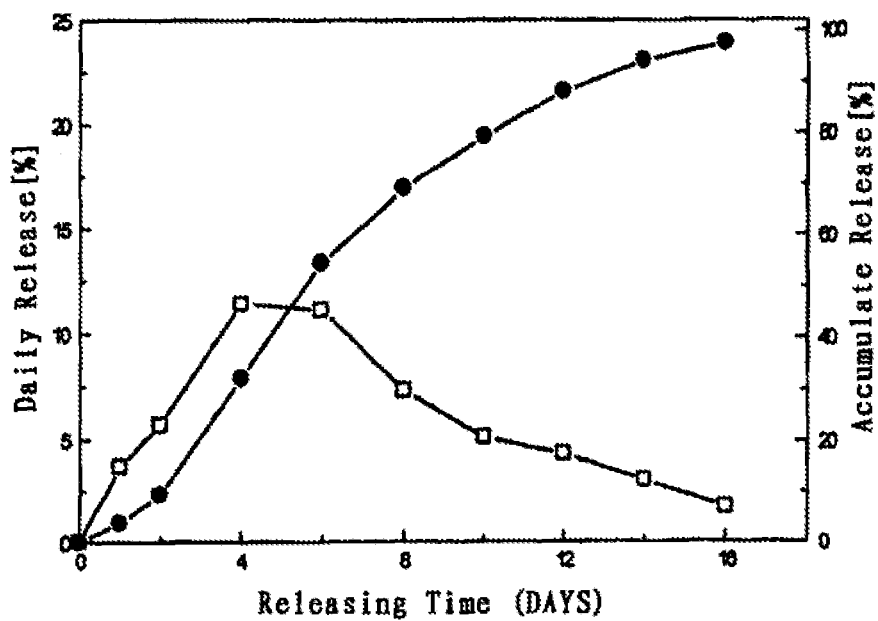
FIG. 6 is the polygonal diagram of daily release rate and accumulative release rate of the sustained-release microspheres obtained in Example 3 in a simulative release liquid having a pH value of 7.4, wherein □ represents daily release, and ● represents accumulative release.
Figure 7:
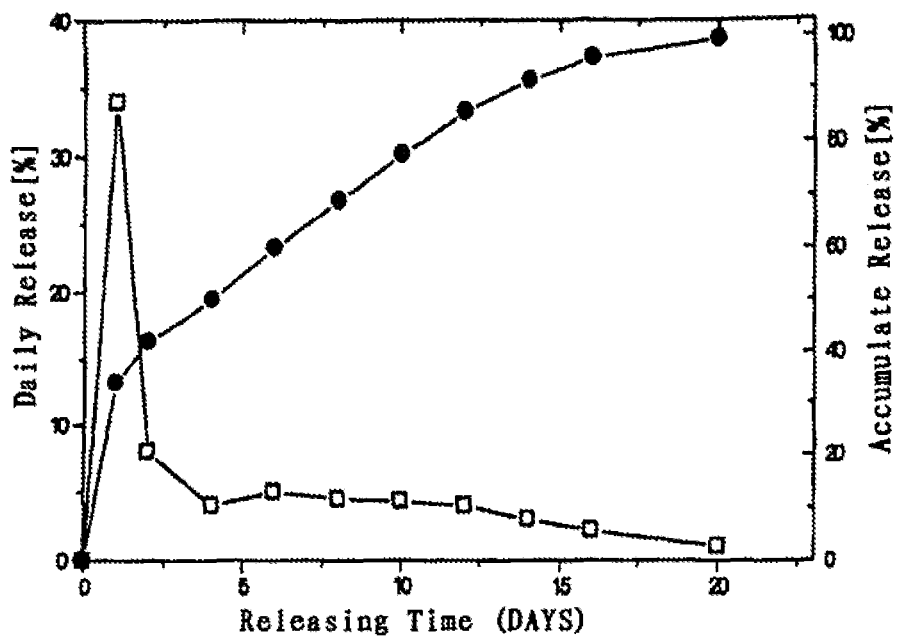
FIG. 7 is the polygonal diagram of daily release rate and accumulative release rate of the sustained-release microspheres obtained in Example 4 in a simulative release liquid having a pH value of 7.4, wherein □ represents daily release, and ● represents accumulative release.
Figure 8:
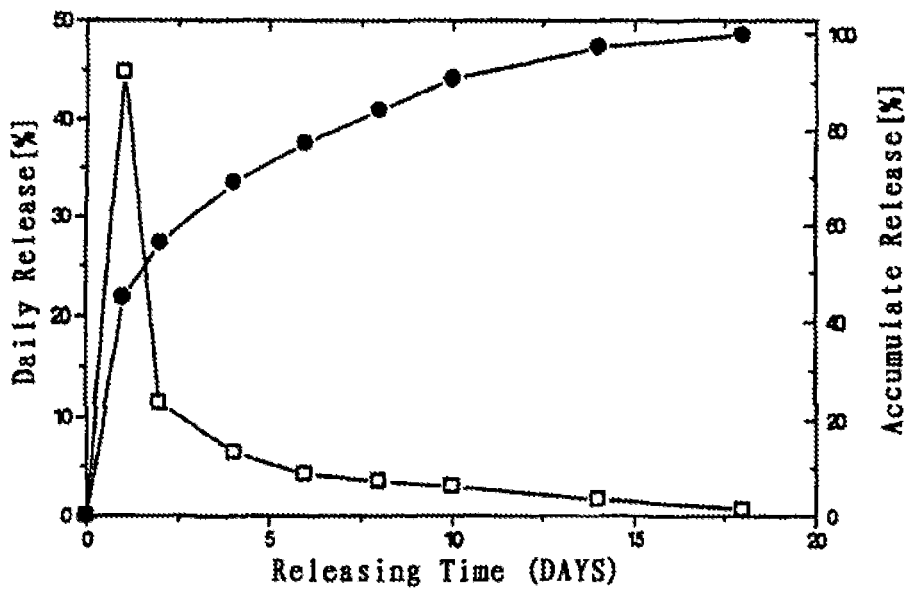
FIG. 8 is the polygonal diagram of daily release rate and accumulative release rate of the sustained-release microspheres obtained in Example 5 in a simulative release liquid having a pH value of 7.4, wherein □ represents daily release, and ● represents accumulative release.
Figure 9:
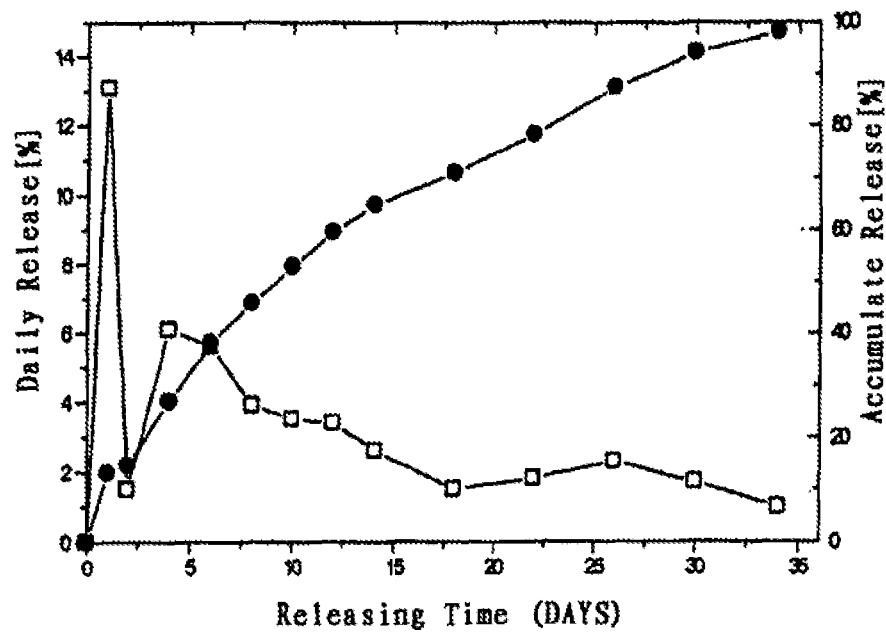
FIG. 9 is the polygonal diagram of daily release rate and accumulative release rate of the sustained-release microspheres obtained in Example 6 in a simulative release liquid having a pH value of 7.4, wherein □ represents daily release, and ● represents accumulative release.

0.1 g of rotigotine and 0.9 g of poly(lactide-glycolide) (lactide:glycolide=50:50, molecular weight=25,000) were dissolved in 5 ml dichloromethane, and then are added dropwise into 250 ml of 0.5% PVA water solution under vigorous agitation (1200-1600 rpm), the vigorous agitation was continued from 3-10 min after the addition was completed, then the agitation rate was reduced to 300 rpm, the solvent was volatilized for 4-6 hours, and microspheres was filtered and washed with distilled water for three times, and freeze-dried. According to the measurement of laser particle size meter, the microspheres had a particle diameter of 1-250 micrometers and a particle diameter distribution as shown in FIG. 2. The scanning electron microscope photo of the microspheres obtained in Example 1 is shown in FIG. 3.

Example 2

Microspheres having 10% drug and a particle diameter of 1-250 micrometers were prepared according to the method of Example 1 by using 0.1 g of rotigotine and 0.9 g of poly(lactide-glycolide) (lactide:glycolide=50:50, molecular weight=13,000). The microspheres passed a screen to remove microspheres having a particle diameter of greater than 150 micrometer, and subpackaged.

Example 3

Microspheres having 20% drug and a particle diameter of 1-250 micrometers were prepared according to the method of Example 1 by using 0.2 g of rotigotine and 0.8 g of poly(lactide-glycolide) (lactide:glycolide=50:50, molecular weight=25,000), wherein 250 ml of 0.5% sodium carboxymethylcellulose water solution was used to replace the 0.5% PVA water solution. The microspheres passed a screen to remove microspheres having a particle diameter of greater than 150 micrometer, and subpackaged.

Example 4

Microspheres having 20% drug and a particle diameter of 1-250 micrometers were prepared according to the method of Example 1 by using 0.2 g of rotigotine and 0.8 g of poly(lactide-glycolide) (lactide:glycolide=75:25, molecular weight=11,000). The microspheres passed a screen to remove microspheres having a particle diameter of greater than 150 micrometer, and subpackaged.

Example 5

0.1 g of rotigotine and 0.9 g of poly(lactide-glycolide) (lactide:glycolide=50:50, molecular weight=25,000) were weighed and dissolved by adding 10 ml dichloromethane under stirring, then atomized into 200 ml petroleum ether by a conventional atomizing method, extracted and filtered, and dried to obtain microspheres. The microspheres had a particle diameter of 1-100 micrometers according to measurement, and then subpackaged.

Example 7

Microspheres having 10% drug and a particle diameter of 1-250 micrometers were prepared according to the method of Example 1 by using 0.1 g of rotigotine and 0.9 g of polycaprolactone (molecular weight=45,000). The microspheres passed a screen to remove microspheres having a particle diameter of greater than 150 micrometer, and subpackaged.

Example 8

Microspheres having 15% drug and a particle diameter of 1-250 micrometers were prepared according to the method of Example 1 by using 0.15 g of rotigotine and 0.85 g of poly-lactic acid) (molecular weight=12,000). The microspheres passed a screen to remove microspheres having a particle diameter of greater than 150 micrometer, and subpackaged.

Example 9

Microspheres having 15% drug and a particle diameter of 1-250 micrometers were prepared according to the method of Example 1 by using 0.15 g of rotigotine and 0.85 g of poly(lactide-glycolide) (lactide:glycolide=50:50, molecular weight=40,000). The microspheres passed a screen to remove microspheres having a particle diameter of greater than 150 micrometer, and subpackaged.

Example 10

Microspheres having 20% drug and a particle diameter of 1-250 micrometers were prepared according to the method of Example 1 by using 0.2 g of rotigotine formate and 0.8 g of poly(lactide-glycolide) (lactide:glycolide=50:50, molecular weight=25,000). The microspheres passed a screen to remove microspheres having a particle diameter of greater than 150 micrometer, and subpackaged.

Example 11

Microspheres having 20% drug and a particle diameter of 1-250 micrometers were prepared according to the method of Example 1 by using 0.2 g of rotigotine acetate and 0.8 g of poly(lactide-glycolide) (lactide:glycolide=50:50, molecular weight=25,000). The microspheres passed a screen to remove microspheres having a particle diameter of greater than 150 micrometer, and subpackaged.

Example 12

Microspheres having 20% drug and a particle diameter of 1-250 micrometers were prepared according to the method of Example 1 by using 0.2 g of rotigotine propionate and 0.8 g of poly(lactide-glycolide) (lactide:glycolide=50:50, molecular weight=25,000). The microspheres passed a screen to remove microspheres having a particle diameter of greater than 150 micrometer, and subpackaged.

Example 13

Microspheres having 20% drug and a particle diameter of 1-250 micrometers were prepared according to the method of Example 1 by using 0.2 g of rotigotine benzoate and 0.8 g of poly(lactide-glycolide) (lactide:glycoiide=50:50, molecular weight=25,000). The microspheres passed a screen to remove microspheres having a particle diameter of greater than 150 micrometer, and subpackaged.

Example 14

Microspheres having 20% drug and a particle diameter of 1-250 micrometers were prepared according to the method of Example 1 by using 0.2 g of rotigotine benzoate and 0.8 g of poly(lactide-glycolide) (lactide:glycolide=50:50, molecular weight=40,000). The microspheres passed a screen to remove microspheres having a particle diameter of greater than 150 micrometer, and subpackaged.

Example 15

Microspheres having 15% drug and a particle diameter of 1-250 micrometers were prepared according to the method of Example 1 by using 0.15 g of ropinirole and 0.85 g of poly(lactide-glycolide) (lactide:glycolide=50:50, molecular weight=25,000). The microspheres passed a screen to remove microspheres having a particle diameter of greater than 150 micrometer, and subpackaged.

Example 16

0.15 g of ropinirole hydrochloride was ground to have an average particle size of less than 1 micrometer, 0.85 g of poly(lactide-glycolide) (lactide:glycolide=50:50, molecular weight=25,000) was dispersed in 5 ml dichloromethane, and the method of Example 1 was employed to prepare microspheres having 15% drug and a particle diameter of 1-250 micrometers. The microspheres passed a screen to remove microspheres having a particle diameter of greater than 150 micrometer, and subpackaged.

Example 17

Microspheres having 15% drug and a particle diameter of 1-250 micrometers were prepared according to the method of Example 1 by using 0.15 g of pramipexole and 0.85 g of poly(lactide-glycolide) (lactide:glycolide=50:50, molecular weight=25,000). The microspheres passed a screen to remove microspheres having a particle diameter of greater than 150 micrometer, and subpackaged.

Example 18

0.15 g of pergolide methanesulfonate was ground to have an average particle size of less than 1 micrometer, 0.85 g of poly(lactide-glycolide) (lactide:glycolide=50:50, molecular weight=25,000) was dispersed in 5 ml dichloromethane, and the method of Example 1 was employed to prepare microspheres having 15% drug and a particle diameter of 1-250 micrometers. The microspheres passed a screen to remove microspheres having a particle diameter of greater than 150 micrometer, and subpackaged.

Example 19

0.15 g of terguride maleate was ground to have an average particle size of less than 1 micrometer, 0.85 g of poly(lactide-glycolide) (lactide:glycolide=50:50, molecular weight=25,000) was dispersed in 5 ml dichloromethane, and the method of Example 1 was employed to prepare microspheres having 15% drug and a particle diameter of 1-250 micrometers. The microspheres passed a screen to remove microspheres having a particle diameter of greater than 150 micrometer, and subpackaged.

Example 20

1 g of rotigotine was dissolved in 1 ml dichloromethane, and sufficiently mixed with 9 g ground polyanhydride (poly (1,3-dicarboxyphenoxypropane-sebacic acid), molecular weight=40,000, average particle diameter=about 200 micrometers), then heated and extruded to prepare a rod-shape implant having 10% drug, a diameter of 1 mm and a length of 30 mm.

Example 21

1 g of dinapsoline hydrobromide was dissolved in 1 ml dichloromethane, and sufficiently mixed with 9 g ground polyanhydride (poly(1,3-dicarboxy-phenoxypropane-sebacic acid), molecular weight=40,000, average particle diameter=about 200 micrometers), then heated and extruded to prepare a rod-shape implant having 10% drug, a diameter of 1 mm and a length of 30 mm.

Example 22

0.15 g rotigotine and 0.85 g poly(lactide-glycolide) (lactide:glycolide=50:50, molecular weight=25,000) were weighed and dissolved in N-methyl pyrrolidone to prepare an injectable gel having a drug load of 15% (where solvent was not taken into account).

Example 23

0.15 g cabergoline diphosphate and 0.85 g poly(lactide-glycolide) (lactide:glycolide=60:40, molecular weight=25,000) were weighed and dissolved in N-methyl pyrrolidone to prepare an injectable gel having a drug load of 15% (where solvent was not taken into account).

Experiment 1: In vitro Release Test (1) of Rotigotine Microspheres

The microspheres of Examples 1 to 6 were used in the release test that stimulated the in vivo conditions.

Figure 13:
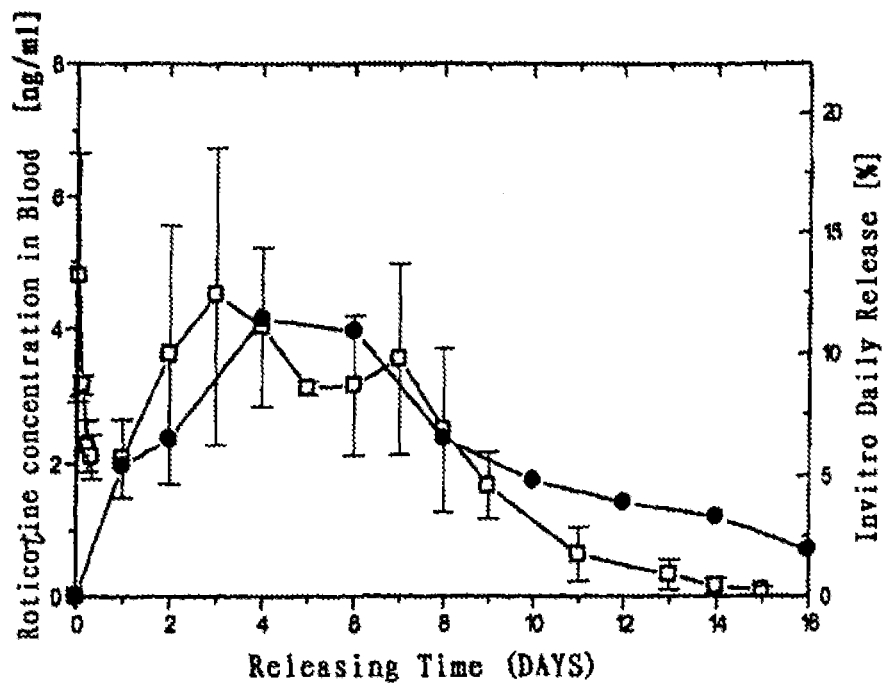
FIG. 13 is the diagram of comparison between the polygonal diagram of daily or accumulative release rate in pH7.4 simulative release liquid and the polygonal diagram of blood rotigotine concentration change in vivo test (beagle) for the sustained-release microspheres obtained in Example 3, wherein □ represents daily release, and ● represents accumulative release.
Figure 14:
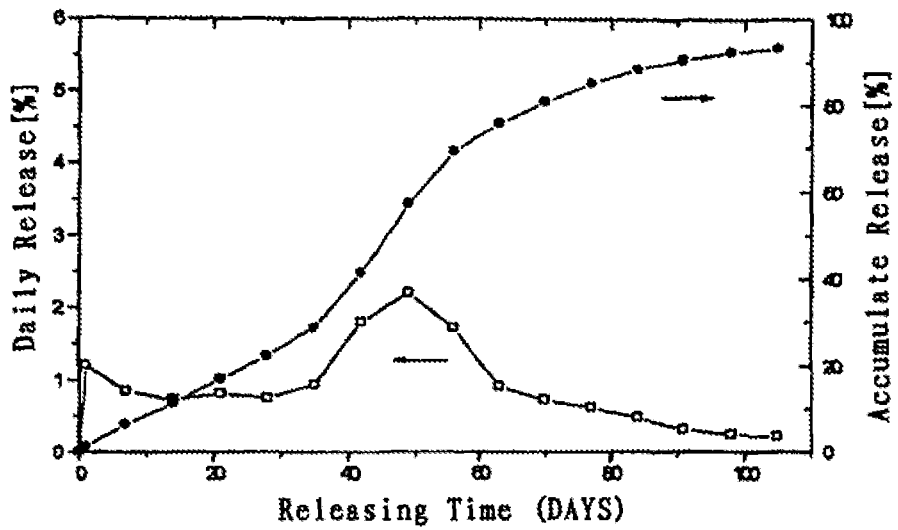
FIG. 14 is the polygonal diagram of daily release rate and accumulative release rate of the implant obtained in Example 20, wherein □ represents daily release, and ● represents accumulative release.
Figure 15:
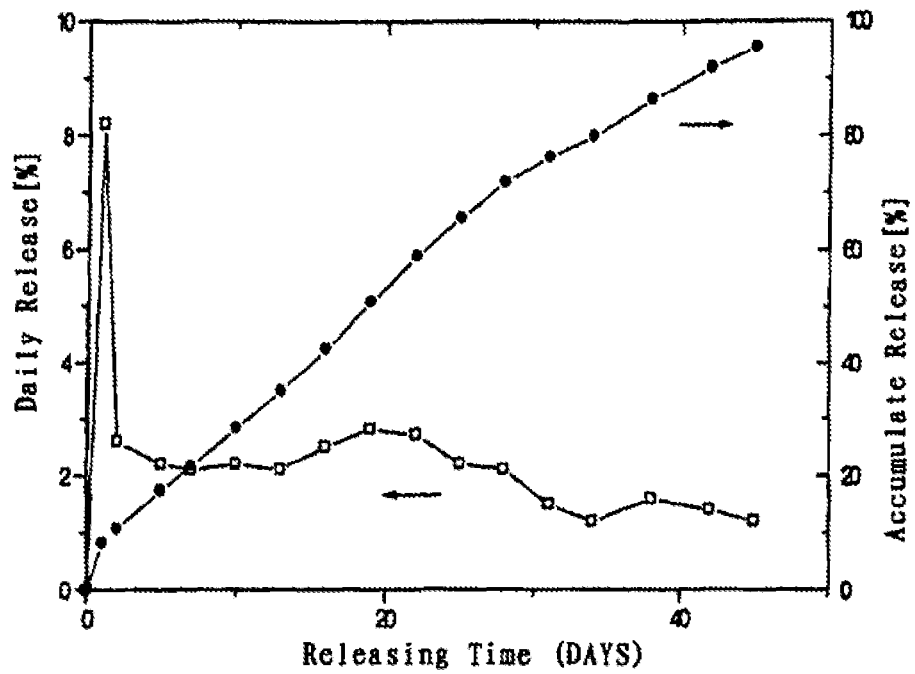
FIG. 15 is the polygonal diagram of daily release rate and accumulative release rate of the injectable gel obtained in Example 22, wherein □ represents daily release, and ● represents accumulative release.

According to the inventors' studying, the drug release behavior in a buffer having a pH value of 7.4 (sodium phosphate buffer) was similar with that in body, so that the in vivo release mode was simulated by using the buffer although it was different from the in vivo environment (see also Experiment 3 and FIG. 13).

Experimental Instrument: thermostatic shaker, centrifugal machine.

Experimental Conditions: temperature=37±0.5° C., rotation speed=30 rpm.

Experimental Methods: precisely weighing about 1 mg of sample, placing in a 5 ml plastic centrifugal tube with lid, adding 5 ml of release medium (pH=7.4, sodium phosphate buffer), keeping at a temperature and a rotation speed in a thermostatic shaker, and sampling according to the schedule.

Sampling methods: centrifuging the centrifugal tube under 3600 rpm for 20 minutes, precisely taking 3 ml solution and supplementing 3 ml of release medium at the same time, and detecting the obtained solution by HPLC.

Sampling time (day): 0, 1, 2, 4, 6, 8, 10, 12, 14, 16, 18, 20, 22 24, 26, 28 and 30 (different microspheres have different sampling time), wherein the $0^{th}$ day represents the drug concentration before the administration on the day when the drug is administrated.

The in vitro release effects of the microspheres of Examples 1-6 under condition of pH7.4 are separately shown in FIGS. 4-9. The experimental results of the microspheres obtained in Examples 1-6 are shown in Table 1.

TABLE 1

| Sample No. | Drug content (μg/mg) | Method for obtaining value | Release percentage (%) | | | | | | | | |
|---|---|---|---|---|---|---|---|---|---|---|---|
| | | | 0 | 1 | 2 | 4 | 6 | 8 | 10 | 12 | 14 |
| Example 1 | 100 | That day | 0 | 5.8 | 1.6 | 1.2 | 2.0 | 3.2 | 3.7 | 3.4 | 3.8 |
| | | Cumulative | 0 | 5.8 | 7.4 | 9.8 | 13.8 | 20.2 | 27.6 | 34.5 | 42.1 |
| Example 2 | 100 | That day | 0 | 11.5 | 11.2 | 6.1 | 6.5 | 5.7 | 5.1 | 4.7 | 3.5 |
| | | Cumulative | 0 | 11.5 | 22.7 | 35.0 | 48.1 | 59.5 | 69.7 | 79.1 | 86.1 |

TABLE 1-continued

| Example 3 | 200 | That day | 0 | 3.7 | 5.7 | 11.4 | 11.1 | 7.3 | 5.1 | 4.3 | 3.0 |
|---|---|---|---|---|---|---|---|---|---|---|---|
|  |  | Cumulative | 0 | 3.7 | 9.4 | 32.2 | 54.4 | 69.0 | 79.2 | 88.0 | 94.0 |
| Example 4 | 200 | That day | 0 | 13.1 | 1.5 | 6.1 | 5.6 | 3.9 | 3.5 | 3.4 | 2.6 |
|  |  | Cumulative | 0 | 13.1 | 14.6 | 26.9 | 38.0 | 45.7 | 52.8 | 59.5 | 64.7 |
| Example 5 | 100 | That day | 0 | 34.0 | 8.0 | 4.0 | 5.0 | 4.5 | 4.3 | 4.0 | 3.5 |
|  |  | Cumulative | 0 | 34.0 | 42.0 | 50.0 | 60.0 | 69.0 | 77.5 | 85.5 | 92.4 |
| Example 6 | 100 | That day | 0 | 44.8 | 11.9 | 6.5 | 4.0 | 3.0 | 2.9 | □ | 1.7 |
|  |  | Cumulative | 0 | 44.8 | 56.7 | 70.7 | 78.7 | 84.7 | 90.5 | □ | 97.2 |

| Sample No. | Drug content (μg/mg) | Method for obtaining value | Release percentage (%) | | | | | | | |
|---|---|---|---|---|---|---|---|---|---|---|
|  |  |  | 16 | 18 | 20 | 22 | 24 | 26 | 28 | 30 |
| Example 1 | 100 | That day | 2.7 | 3.1 | 3.5 | 3.5 | 4.2 | 3.6 | 3.1 | 1.9 |
|  |  | Cumulative | 47.5 | 53.6 | 58.8 | 65.8 | 72.7 | 81.0 | 94.3 | 98.0 |
| Example 2 | 100 | That day | □ | 1.8 | □ | 1.5 |  |  |  |  |
|  |  | Cumulative | □ | 93.3 | □ | 99.3 |  |  |  |  |
| Example 3 | 200 | That day | 1.7 |  |  |  |  |  |  |  |
|  |  | Cumulative | 97.4 |  |  |  |  |  |  |  |
| Example 4 | 200 | That day | □ | 1.5 | □ | 1.8 | □ | 2.3 | □ | 1.7 |
|  |  | Cumulative | □ | 70.9 | □ | 78.2 | □ | 87.4 | □ | 94.2 |
| Example 5 | 100 | That day | □ | 1.8 | □ | 1.0 |  |  |  |  |
|  |  | Cumulative | □ | 95.8 | □ | 100 |  |  |  |  |
| Example 6 | 100 | That day | □ | 0.65 |  |  |  |  |  |  |
|  |  | Cumulative | □ | 99.8 |  |  |  |  |  |  |

Note: the release on that day in the table is calculated from the cumulative release until that day; concretely, it is assumed that the drug release rate during the period between the two measurements is unchanged. As expressed by a formula, the release on that day=(the cumulative release on that day−the cumulative release obtained by the previous measurement)÷the number of days between the day for the previous measurement and that day.

Taking Example 1 as example, the release on the $0^{th}$ day is 0, the cumulative release on the $1^{st}$ day is 5.8, so that the release on the $1^{st}$ day=(5.8−0)÷(1−0)=5.8; the release on the $2^{nd}$ day is 7.4, so that the release on the $2^{nd}$ day=(7.4−5.8)÷(2−1)=1.6; and the release on the $4^{th}$ day is 9.8, so that the release on the $4^{th}$ day=(9.8−7.4)÷(4−2)=1.2. The rest may be deduced by analogy.

According to the table, the sustained-release microspheres of rotigotine of the present invention has a stable release within the period of more than two weeks. Thus, the administration frequency for patients with Parkinson Disease can be reduced significantly, the dosage can be effectively controlled, and side-effects are avoided.

Experiment 2: In vitro Release Test 2 of Rotigotine Microspheres

The microspheres of Examples 11 and 13 were measured according to the same method of Experiment 2, except that the sampling time (day) was: 0, 1, 2, 4, 6, 8, 12, 14, 18, 20, 22, 24, 26, 28, 30, 32, 34, 36 and 38.

Figure 10:
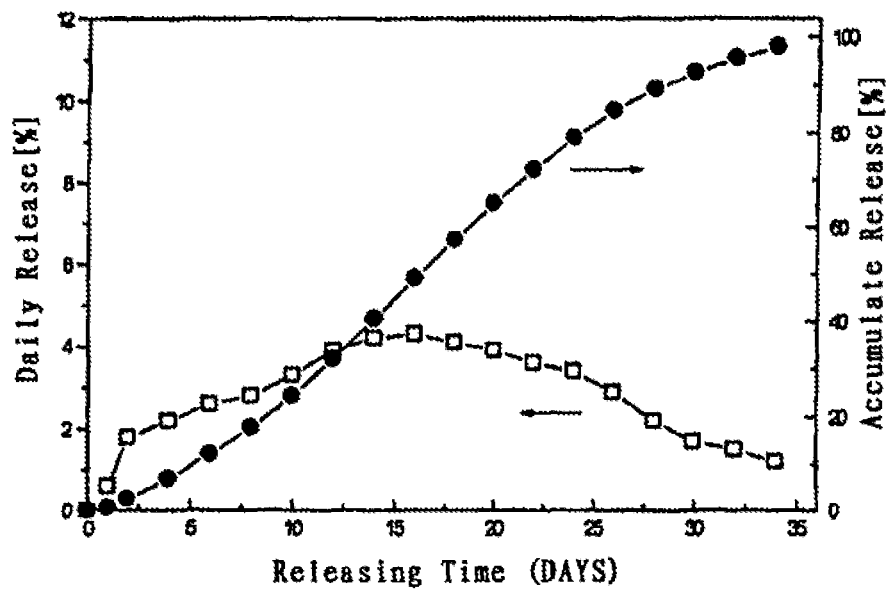
FIG. 10 is the polygonal diagram of daily release rate and accumulative release rate of the sustained-release microspheres obtained in Example 11 in a simulative release liquid having a pH value of 7.4, wherein □ represents daily release, and ● represents accumulative release.
Figure 11:
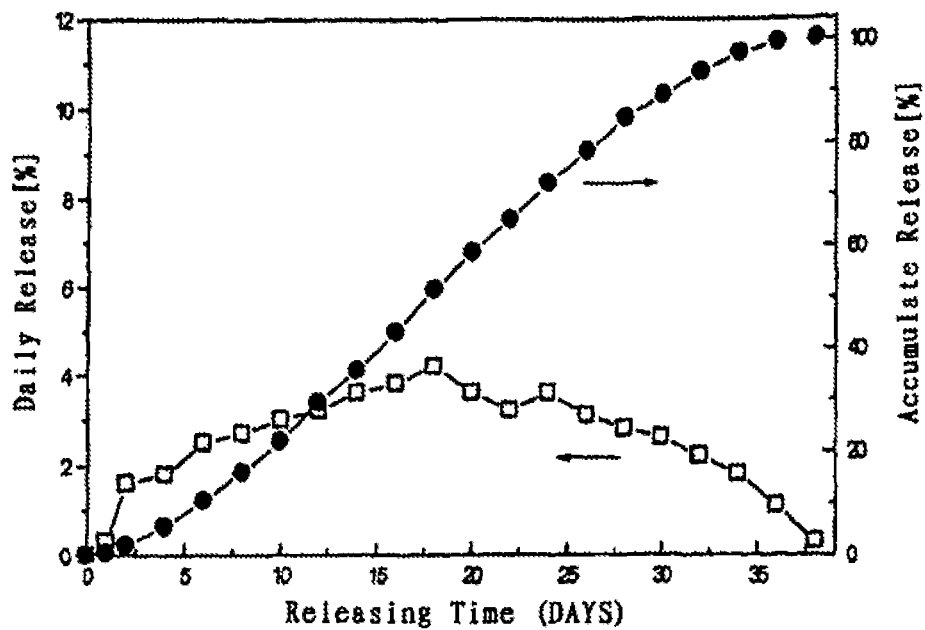
FIG. 11 is the polygonal diagram of daily release rate and accumulative release rate of the sustained-release microspheres obtained in Example 13 in a simulative release liquid having a pH value of 7.4, wherein □ represents daily release, and ● represents accumulative release.

The in vitro release effects of the microspheres of Examples 11 and 13 under condition of pH7.4 are separately shown in FIGS. 10 and 11.

Experiment 3: In vivo Release Test of Sustained-release Microspheres Analysis of Plasma Samples Pretreatment of plasma samples: precisely taking 500 μL of plasma sample and placing it in a test tube, adding 100 μL of an internal standard solution (1 ng/mL benadryl methanol-water (50:50, v/v) solution), adding 100 μL methanol-water (50:50, v/v) and 100 μL 1M $Na_2CO_3$ solution, and mixing homogeneously; adding 3 mL, n-hexane-dichloromethane-isopropanol (300:150:15, v/v/v), mixing at eddy current state for 1 minute, reciprocally shaking for 15 minutes (240/min), centrifuging for 5 minutes (3500 rpm), transferring the organic phase as upper layer into another test tube, blowing nitrogen gas and drying at 25° C., dissolving the residue by adding 100 μL mobile phase, mixing under eddy current state, and taking 20 μL, for LC/MS/MS analysis.

Chromatography Conditions: chromatography column: Zorbax Extend-$C_{18}$ column, 5 μm of particle diameter, 150× 4.6 mm I.D. (Agilent Company, U.S.A.); mobile phase: acetonitrile-water-formic acid (300:300:6, v/v/v); flow rate: 0.7 mL/min; column temperature: 37° C.; sample size: 20 μL.

Mass spectrum conditions: ion source: ion-spray ionizing source; ion-spray voltage: 5000V; temperature: 450° C.; internal source gas 1 (GS1, $N_2$) pressure: 50 psi; gas 2 (GS2, $N_2$) pressure: 50 psi; gas-curtain gas ($N_2$) pressure: 15 psi; positive ion detection mode; scanning mode: multiple reaction monitoring (MRM); DP voltage: 56V; impact gas ($N_2$) pressure: 3 psi; the ion reactions for quantitative analysis are separately m/z 317.1→m/z 147.1(MD102) and m/z 256.1→m/z 167.1 (benadryl).

Preparation of working curve: taking 0.5 mL blank plasma, adding 100 μL of MD102 standard serial solution, preparing plasma samples corresponding to plasma concentrations of 0.01, 0.03, 0.10, 0.30, 1.00 and 2.00 ng/mL; and preparing standard curve according to the "Methods for analysis of plasma sample" of Section II of the Pharmacopoeia of People's Republic of China, Edition 2000. The linear regression equation as the standard curve is obtained by using the concentration of the substance to be tested in plasma as abscissa, the peak area ratio of the substance to be test to the internal standard as ordinate, and conducting regression calculation by using a weighted least square method (W=1/$x^2$).

Experimental Method:

3 Healthy beagles, one female and two males, having a body weight of 9-11 kg, feeding and drinking water ad libitum, were intramuscularly administrated with rotigotine in a dosage of 5.5 mg/kg, and 3 mL blood sample was taken from anterior limb vein according to the prescribed schedule after the administration, placed in heparinized test tube, and centrifuged under 6000 rpm for 10 min, then the plasma was separated and preserved at −20° C., and analyzed according to the above analysis methods.

Figure 12:
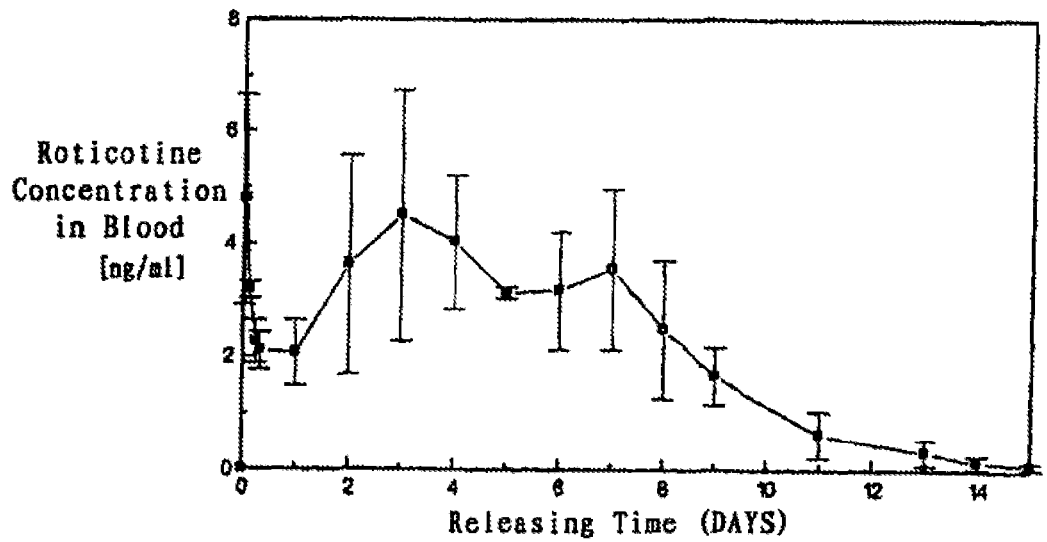
FIG. 12 is the polygonal diagram of blood rotigotine concentration change in vivo test (beagle) for the microspheres obtained in Example 3.

FIG. 12 is the polygonal diagram of blood rotigotine concentration change in vivo test (beagle) for the microspheres obtained in Example 3.

FIG. 13 is the diagram of comparison between the polygonal diagram of daily or accumulative release rate in pH7.4 simulative release liquid and the polygonal diagram of blood rotigotine concentration change in vivo test (beagle) for the sustained-release microspheres obtained in Example 3.

According to FIG. 12, it can be seen that the drug release of the microspheres of the present invention is stable for at least two weeks.

Experiment 4: In vitro Release Test of Implants

Experimental Method:

Experimental Instrument: thermostatic shaker, centrifugal machine.

Experimental Conditions: temperature =37±0.5° C., rotation speed=30 rpm.

Experimental Methods: precisely weighing about 0.1 g of the implant of Example 20, placing in a 5 ml plastic centrifugal tube with lid, adding 5 ml of release medium (pH=7.4, sodium phosphate buffer), keeping at a temperature and a rotation speed in a thermostatic shaker, sampling 3 ml according to the schedule and supplementing 3 ml of the release medium.

Sampling time (day): 0, 1, 7, 14, 21, 28, 35, 42, 49, 56, 63, 70, 77, 94, 91, 98 and 105, wherein the $0^{th}$ day represents the drug concentration before the administration on the day when the drug is administrated. The results are shown in Table 2.

TABLE 2

| Sample No. | Method for obtaining value | Release percentage (%) | | | | | | | | |
|---|---|---|---|---|---|---|---|---|---|---|
| | | 0 | 1 | 7 | 14 | 21 | 28 | 5 | 42 | 49 |
| Example 20 | That day | 0 | 1.2 | 0.84 | 0.72 | 0.81 | 0.75 | 0.94 | 1.8 | 2.2 |
| | Cumulative | 0 | 1.2 | 6.24 | 11.28 | 16.95 | 22.2 | 28.78 | 41.38 | 57.23 |
| | Method for obtaining value | Release percentage (%) | | | | | | | | |
| | | 56 | 63 | 70 | 77 | 84 | 91 | 98 | 105 | |
| | That day | 1.72 | 0.91 | 0.72 | 0.62 | 0.48 | 0.32 | 0.25 | 0.22 | |
| | Cumulative | 69.27 | 75.64 | 80.68 | 85.02 | 88.38 | 90.62 | 92.37 | 93.31 | |

According to the results of above experiment, the implant of the present invention can continuously release drug for more than two months.

Experiment 5: In vitro Release Test of Injectable Gel

Experimental Method:

Experimental Instrument: thermostatic shaker, centrifugal machine.

Experimental Conditions: temperature=37±0.5° C., rotation speed=30 rpm.

Experimental methods: precisely weighing about 0.1 mL of the injectable gel obtained in Example 22, placing in a 5 ml plastic centrifugal tube with lid, adding 5 ml of release medium (pH=7.4, sodium phosphate buffer), keeping at a temperature and a rotation speed in a thermostatic shaker, sampling 3 ml according to the schedule and supplementing 3 ml of the release medium.

Sampling time (day): 0, 1, 2, 5, 7, 10, 13, 16, 19, 22, 25, 28, 31, 34, 38, 42, 45, wherein the $0^{th}$ day represents the drug concentration before the administration on the day when the drug is administrated. The results are shown in Table 3.

TABLE 3

| Sample No. | Method for obtaining value | Release percentage (%) | | | | | | | | |
|---|---|---|---|---|---|---|---|---|---|---|
| | | 0 | 1 | 2 | 5 | 7 | 10 | 13 | 16 | 19 |
| Example 22 | That day | 0 | 8.2 | 2.6 | 2.2 | 2.1 | 2.2 | 2.1 | 2.5 | 2.8 |
| | Cumulative | 0 | 8.2 | 10.8 | 17.4 | 21.6 | 28.2 | 34.8 | 42.3 | 50.7 |
| | Method for obtaining value | Release percentage (%) | | | | | | | | |
| | | 22 | 25 | 28 | 31 | 34 | 38 | 42 | 45 | |
| | That day | 2.7 | 2.2 | 2.1 | 1.5 | 1.2 | 1.6 | 1.4 | 1.2 | |
| | cumulative | 58.8 | 65.4 | 71.7 | 76.2 | 79.8 | 86.2 | 91.8 | 95.4 | |

According to the results of the above experiment, the gel of the present invention can continuously release drug for more than 45 days.

Example 24

Microspheres having 8% drug (actually having 7.8% drug) and a particle diameter of 1-250 micrometers were prepared according to the method of Example 1 by using 0.08 g of rotigotine and 0.92 g of poly(lactide-glycolide) (lactide:glycolide=50:50, molecular weight=25,000). The microspheres passed a screen to remove microspheres having a particle diameter of greater than 180 micrometer, and subpackaged.

Figure 16:
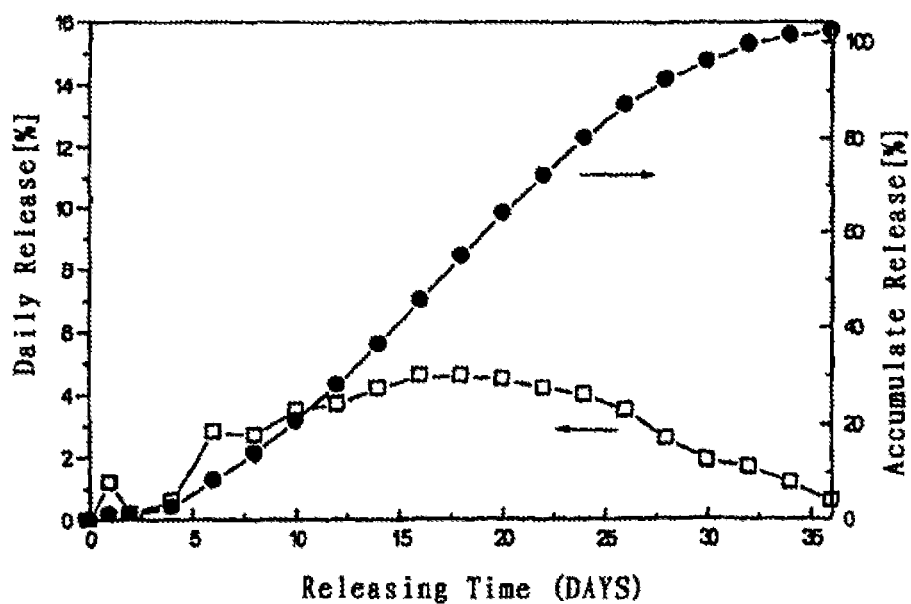
FIG. 16 is the polygonal diagram of daily release rate and accumulative release rate of the rotigotine microspheres (actually containing 7.8% of active component) obtained in Example 24 in a simulative release liquid having a pH value of 7.4, wherein □ represents daily release, and ● represents accumulative release.

The in vitro release effect of the rotigotine microspheres (actually having 7.8% thug) under condition of pH7.4 is shown in FIG. 16.

The sustained-release microspheres were administrated to beagle for in vivo release test, wherein the dosage of rotigotine was 2.75 mg/kg (by assuming the body weight of beagle as 10 kg, the dosage corresponds to 1150 mg microspheres having 7.8% drug that is injected one time to an adult human being having a body weight of 65 kg). The microspheres were suspended in physiological saline and administrated intramuscularly, and blood samples were taken between 1 and 30 days and detected by HPLC-MS assay to indicate a blood drug level of 0.05-0.4 ng/ml. This proves that the sustained-release microspheres can stably release drug for at least 30 days, although the blood drug concentration is relatively lower and can hardly meet the requirement of blood drug concentration (>0.5 ng/mL) for treatment of Parkinson Disease of patients, especially those in evaluation period, while the increase of dosage means overdose injection that may lead to complaint and suffering in patients.

Figure 17:
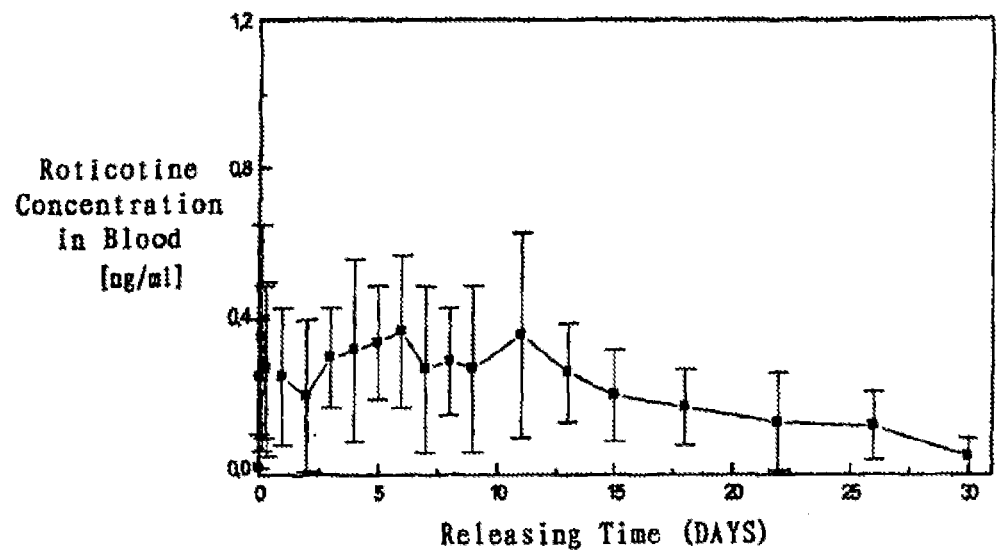
FIG. 17 is the polygonal diagram of blood rotigotine concentration change in vivo test (beagle) for the rotigotine microspheres obtained in Example 24.

FIG. 17 is the polygonal diagram of blood rotigotine concentration change in vivo test (beagle) for the rotigotine microspheres (actually having 7.8% drug) obtained in Example 24.

Example 25

Microspheres having 30% drug (actually having 26.5% drug) and a particle diameter of 1-250 micrometers were prepared according to the method of Example 1 by using 0.30 g of rotigotine and 0.70 g of poly(lactide-glycolide) (lactide:glycolide=50:50, molecular weight=45,000). The microspheres passed a screen to remove microspheres having a particle diameter of greater than 200 micrometer, and subpackaged.

Figure 18:
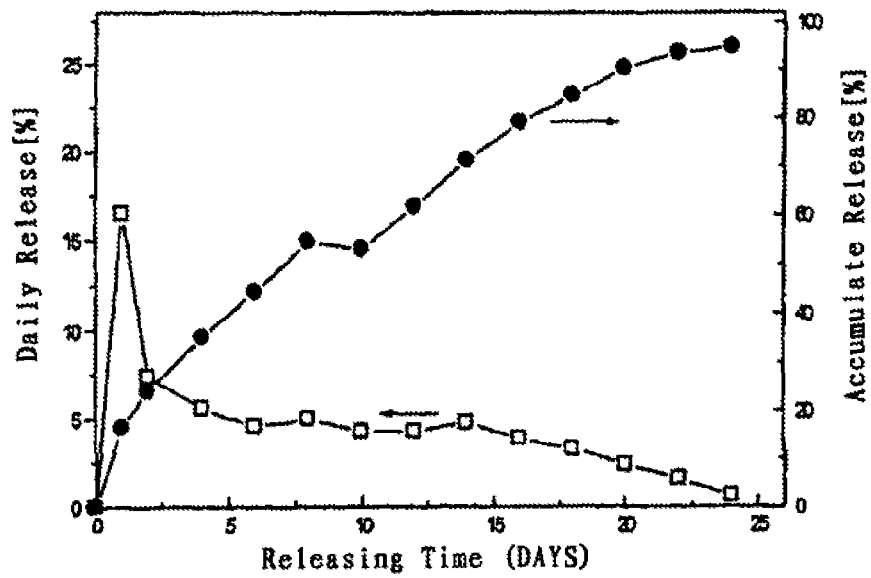
FIG. 18 is the polygonal diagram of daily release rate and accumulative release rate of the rotigotine microspheres (actually containing 26.5% of active component) obtained in Example 25 in a simulative release liquid having a pH value of 7.4, wherein □ represents daily release, and ● represents accumulative release.

The in vitro release effect of the rotigotine microspheres (actually having 26.5% drug) under condition of pH7.4 is shown in FIG. 18.

Example 26

Microspheres having 40% drug (actually having 34% drug) and a particle diameter of 1-250 micrometers were prepared according to the method of Example 1 by using 0.4 g of rotigotine and 0.6 g of poly(lactide-glycolide) (lactide:glycolide=50:50, molecular weight=45,000). The microspheres passed a screen to remove microspheres having a particle diameter of greater than 200 micrometer, and subpackaged.

Figure 19:
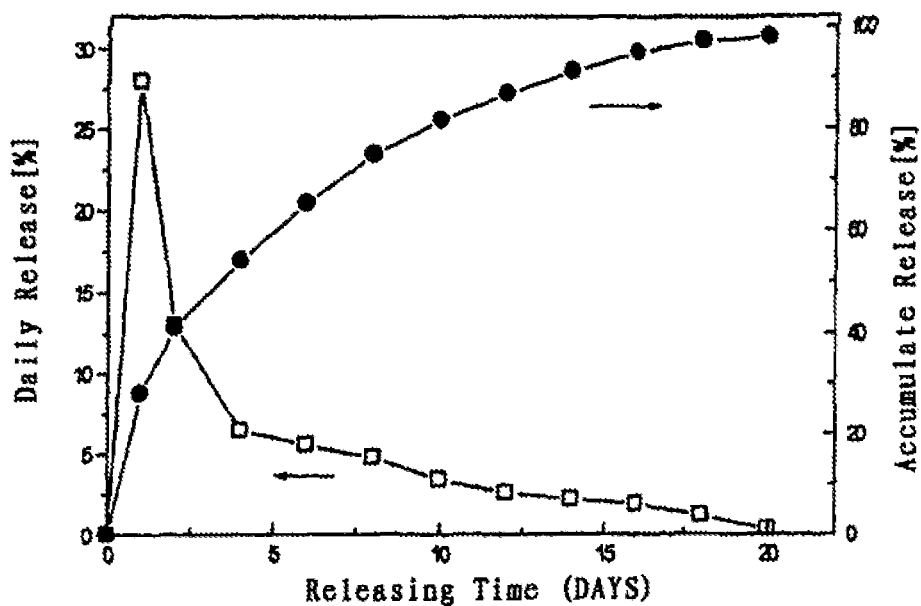
FIG. 19 is the polygonal diagram of daily release rate and accumulative release rate of the rotigotine microspheres (actually containing 34% of active component) obtained in Example 26 in a simulative release liquid having a pH value of 7.4, wherein □ represents daily release, and ● represents accumulative release.

The in vitro release effect of the rotigotine microspheres (actually having 34% drug) under condition of pH7.4 is shown in FIG. 19.

The sustained-release microspheres were administrated to beagle for in vivo release test, wherein the dosage of rotigotine was 5.5 mg/kg (by assuming the body weight of beagle as 10 kg, the dosage corresponds to 520 mg microspheres having 34% drug that is injected one time to an adult human being having a body weight of 65 kg). The microspheres were suspended in physiological saline and administrated intramuscularly, and blood samples were taken between 1 and 11 days and detected by HPLC-MS assay to indicate a blood drug level of 28-0.05 ng/ml. The results show that when the drug load is relatively higher (>30%), the initial release of microspheres within 24 hours is relatively high, which results in the side-effects such as intensive emesis and so on in animal, the blood drug level decreases quickly with the increase of time, and the sustained-release effects are not good.

Figure 20:
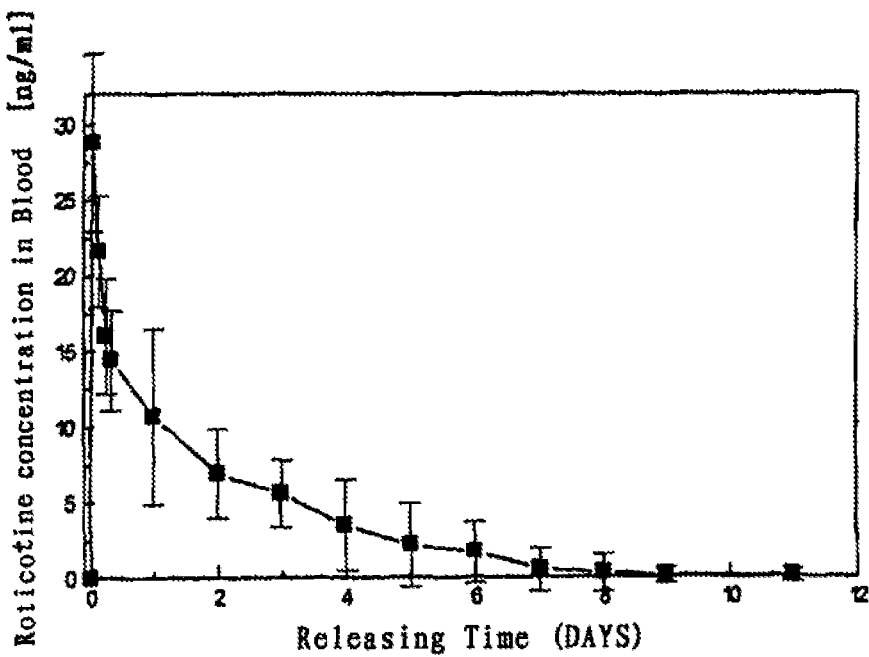
FIG. 20 is the polygonal diagram of blood rotigotine concentration change in vivo test (beagle) for the rotigotine microspheres obtained in Example 26.

FIG. 20 is the polygonal diagram of blood rotigotine concentration change in vivo test (beagle) for the rotigotine microspheres (actually having 34% drug) obtained in Example 26.

Example 27

Microspheres having 50% drug (actually having 41% drug) and a particle diameter of 1-250 micrometers were prepared according to the method of Example 1 by using 0.50 g of rotigotine and 0.50 g of poly(lactide-glycolide) (lactide:glycolide=50:50, molecular weight=45,000). The microspheres passed a screen to remove microspheres having a particle diameter of greater than 200 micrometer, and subpackaged.

Figure 21:
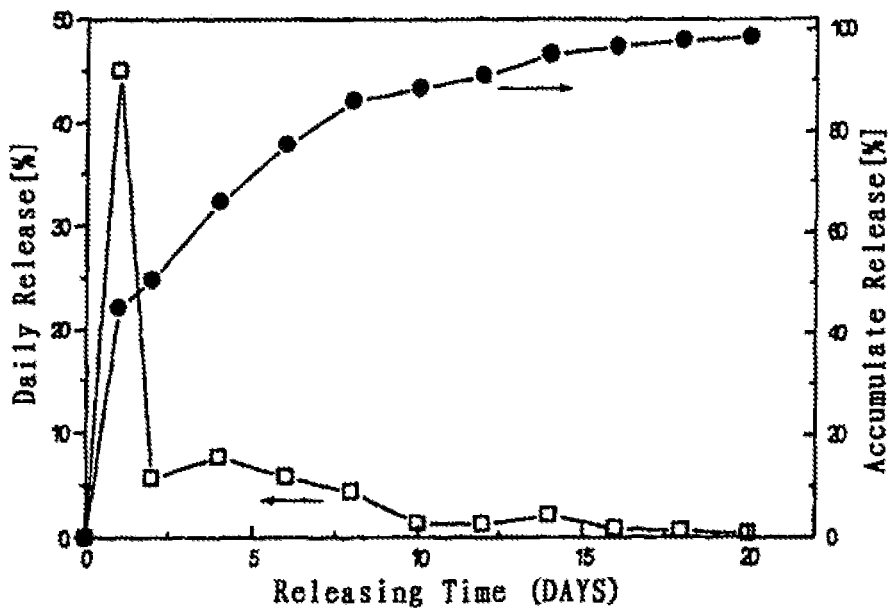
FIG. 21 is the polygonal diagram of daily release rate and accumulative release rate of the rotigotine microspheres (actually containing 41% of active component) obtained in Example 27 in a simulative release liquid having a pH value of 7.4, wherein □ represents daily release, and ● represents accumulative release.

The in vitro release effect of the rotigotine microspheres (actually having 41% drug) under condition of pH7.4 is shown in FIG. 21.

Example 28

Microspheres having 50% drug (actually having 43% drug) and a particle diameter of 1-250 micrometers were prepared according to the method of Example 1 by using 0.50 g of rotigotine and 0.50 g of poly(lactide-glycolide) (lactide:glycolide=50:50, molecular weight=35,000). The microspheres passed a screen to remove microspheres having a particle diameter of greater than 200 micrometer, and subpackaged.

Figure 22:
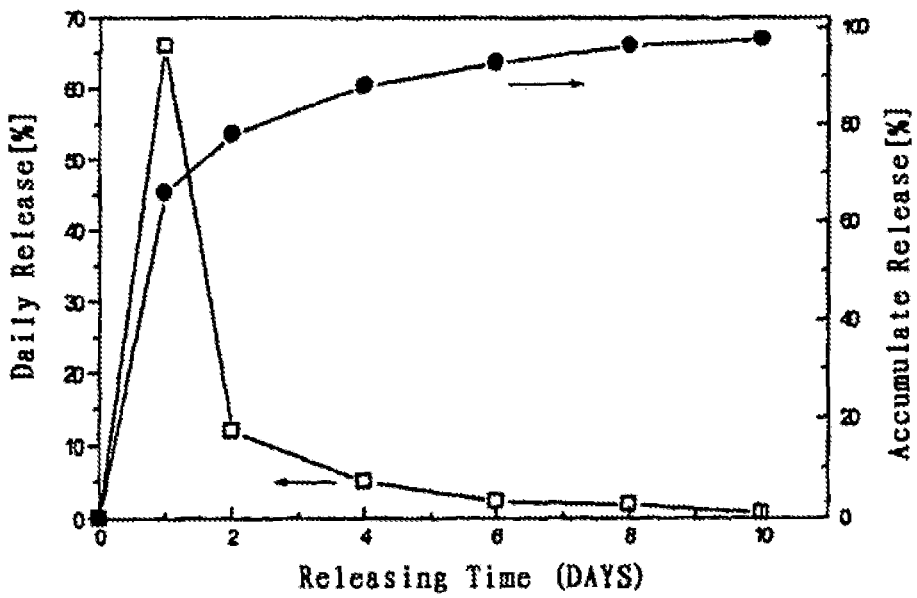
FIG. 22 is the polygonal diagram of daily release rate and accumulative release rate of the rotigotine microspheres (actually containing 43% of active component) obtained in Example 28 in a simulative release liquid having a pH value of 7.4, wherein □ represents daily release, and ● represents accumulative release.

The in vitro release effect of the rotigotine microspheres (actually having 43% drug) under condition of pH7.4 is shown in FIG. 22.

Example 29

Microspheres having 60% drug (actually having 47% drug) and a particle diameter of 1-250 micrometers were prepared according to the method of Example 1 by using 0.60 g of rotigotine and 0.40 g of poly(lactide-glycolide) (lactide:glycolide=50:50, molecular weight=45,000). The microspheres passed a screen to remove microspheres having a particle diameter of greater than 200 micrometer, and subpackaged.

Figure 23:
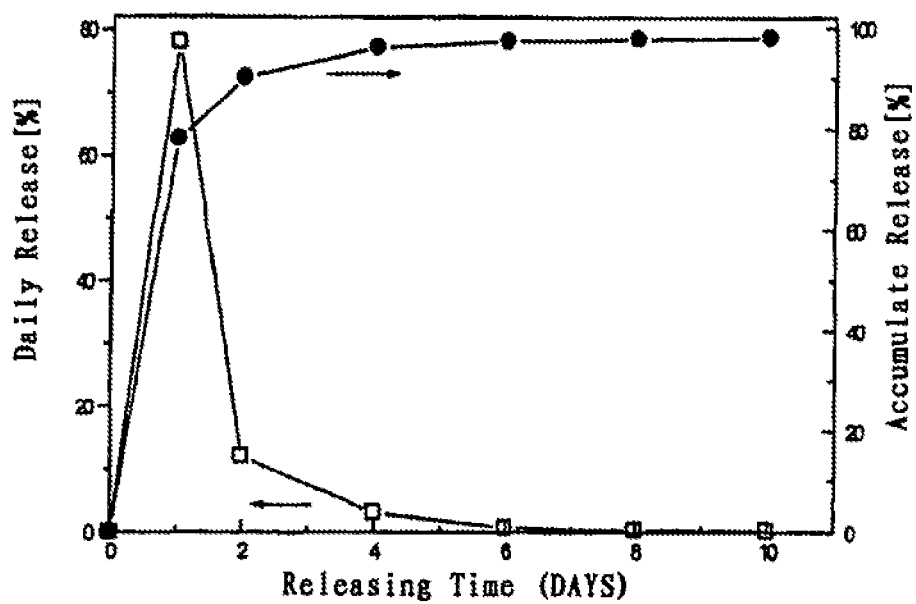
FIG. 23 is the polygonal diagram of daily release rate and accumulative release rate of the rotigotine microspheres (actually containing 47% of active component) obtained in Example 29 in a simulative release liquid having a pH value of 7.4, wherein □ represents daily release, and ● represents accumulative release.

The in vitro release effect of the rotigotine microspheres (actually having 47% drug) under condition of pH7.4 is shown in FIG. 23.

Industrial Practical Applicability

The present invention employs biodegradable polymer to embed dopamine receptor agonist in order to prepare long-acting sustained-release dosage forms, such as injectable microspheres, injectable gels and implants, which have an administration interval of more than two weeks, in particular, the implants have an administration interval of more than one month, so that the present invention greatly facilitates the administration for patients having Parkinson Disease and other dopamine receptor-associated diseases.

The invention claimed is:

1. A method of treating Parkinson disease in a patient in need thereof comprising administering to the patient a long-acting sustained release formulation comprising:
   (1) rotigotine or a pharmaceutically acceptable salt thereof; and
   (2) poly(lactide-glycolide),
   wherein rotigotine or a pharmaceutically acceptable salt thereof is present in the sustained-release formulation at 10-30% by weight, and poly(lactide-glycolide) is present in the sustained-release formulation at 70-90% by weight, and wherein the rotigotine or a pharmaceutically acceptable salt thereof and poly(lactide-glycolide) form a solid solution.

2. The method of claim 1 wherein administering comprises injecting the long-acting sustained-release formulation as microspheres or a gel.

3. The method of claim 1 wherein administering comprises subcutaneously implanting the long-acting sustained-release formulation.

4. The method of claim 1 wherein said poly(lactide-glycolide) has a molecular weight of 5,000-100,000 daltons.

5. The method of claim 4, wherein the polymerization ratio of lactide to glycolide in the poly(lactide-glycolide) is between 95:5 and 5:95.

6. The method of claim 4 wherein the polymerization ratio of lactide to glycolide in the poly(lactide-glycolide) is between 75:25 and 25:75.

7. The method of claim 2 wherein the long-acting sustained-release formulation is an injectable composition of sustained-release microspheres, the microspheres having particle, diameters of 50 to 200 microns.

8. The method of claim 1 wherein the pharmaceutically acceptable salt of rotigotine is a salt formed between the active ingredient and an inorganic acid, an organic, acid or an acidic amino acid.

9. The method of claim 8 wherein the inorganic acid is hydrochloric acid, sulfuric acid, phosphoric acid or nitric acid; the organic acid is citric, acid, fumaric acid, maleic acid, acetic acid, benzoic acid, methane sulfonic acid, naphthalene sulfonic acid, or p-toluene sulfonic acid; and the acidic amino acid is glutamic acid or aspartic acid.

10. The method of claim 1 wherein said rotigotine or pharmaceutically acceptable salt is rotigotine, rotigotine formate, rotigotine acetate, rotigotine benzoate, rotigotine butyrate, rotigotine iso-butyrate or a hydrochloride thereof.

* * * * *